United States Patent
Jacquel et al.

(10) Patent No.: US 11,350,850 B2
(45) Date of Patent: *Jun. 7, 2022

(54) SYSTEMS AND METHODS FOR VIDEO-BASED MONITORING OF VITAL SIGNS

(71) Applicant: Covidien LP, Mansfield, MA (US)

(72) Inventors: Dominique Jacquel, Edinburgh (GB); Paul Stanley Addison, Edinburgh (GB); David Foo, Glasgow (GB)

(73) Assignee: Covidien, LP, Mansfield, MA (US)

( * ) Notice: Subject to any disclaimer, the term of this patent is extended or adjusted under 35 U.S.C. 154(b) by 53 days.

This patent is subject to a terminal disclaimer.

(21) Appl. No.: 16/874,325

(22) Filed: May 14, 2020

(65) Prior Publication Data

US 2020/0268281 A1  Aug. 27, 2020

Related U.S. Application Data

(63) Continuation of application No. 15/432,057, filed on Feb. 14, 2017, now Pat. No. 10,667,723.

(Continued)

(51) Int. Cl.
*A61B 5/103* (2006.01)
*A61B 5/00* (2006.01)
(Continued)

(52) U.S. Cl.
CPC .......... *A61B 5/1032* (2013.01); *A61B 5/0077* (2013.01); *A61B 5/0205* (2013.01);
(Continued)

(58) Field of Classification Search
CPC ..... A61B 5/743; A61B 5/7485; A61B 5/7221; A61B 5/441; A61B 5/1176; A61B 5/748;
(Continued)

(56) References Cited

U.S. PATENT DOCUMENTS

| 5,107,845 A | 4/1992 | Guern et al. |
| 5,408,998 A | 4/1995 | Mersch |

(Continued)

FOREIGN PATENT DOCUMENTS

| CN | 106725410 A | 5/2017 |
| CN | 111728602 A | 10/2020 |

(Continued)

OTHER PUBLICATIONS

Hyvarinen, A. et al., "Independent Component Analysis: Algorithms and Applications", Neural Networks, vol. 13, No. 4, 2000, pp. 411-430, 31 pages.

(Continued)

*Primary Examiner* — Brenda C Bernardi
(74) *Attorney, Agent, or Firm* — Holzer Patel Drennan

(57) ABSTRACT

The present invention relates to the field of medical monitoring, and in particular non-contact, video-based monitoring of pulse rate, respiration rate, motion, and oxygen saturation. Systems and methods are described for capturing images of a patient, producing intensity signals from the images, filtering those signals to focus on a physiologic component, and measuring a vital sign from the filtered signals. Examples include flood fill methods and skin tone filtering methods.

20 Claims, 23 Drawing Sheets

Related U.S. Application Data

(60) Provisional application No. 62/399,741, filed on Sep. 26, 2016, provisional application No. 62/335,862, filed on May 13, 2016, provisional application No. 62/297,682, filed on Feb. 19, 2016.

(51) Int. Cl.
    *A61B 5/024*      (2006.01)
    *A61B 5/1171*      (2016.01)
    *A61B 5/1455*      (2006.01)
    *A61B 5/0205*      (2006.01)
    *A61B 5/145*      (2006.01)
    *A61B 5/08*      (2006.01)

(52) U.S. Cl.
CPC ........ *A61B 5/02416* (2013.01); *A61B 5/1176* (2013.01); *A61B 5/14542* (2013.01); *A61B 5/14551* (2013.01); *A61B 5/441* (2013.01); *A61B 5/6843* (2013.01); *A61B 5/7203* (2013.01); *A61B 5/7221* (2013.01); *A61B 5/7278* (2013.01); *A61B 5/743* (2013.01); *A61B 5/746* (2013.01); *A61B 5/748* (2013.01); *A61B 5/7425* (2013.01); *A61B 5/7485* (2013.01); *A61B 5/024* (2013.01); *A61B 5/0816* (2013.01); *A61B 2562/0233* (2013.01); *A61B 2576/00* (2013.01)

(58) Field of Classification Search
CPC . A61B 5/14551; A61B 5/7203; A61B 5/6843; A61B 5/14542; A61B 5/7425; A61B 5/746; A61B 5/0077; A61B 5/02416; A61B 5/1032; A61B 5/7278; A61B 2576/00; A61B 2562/0233; A61B 5/024; A61B 5/0816
See application file for complete search history.

(56) References Cited

U.S. PATENT DOCUMENTS

| | | | |
|---|---|---|---|
| 5,704,367 A | 1/1998 | Ishikawa et al. | |
| 5,800,360 A | 9/1998 | Kisner et al. | |
| 5,995,856 A | 11/1999 | Mannheimer et al. | |
| 6,668,071 B1 | 12/2003 | Minkin et al. | |
| 6,920,236 B2 | 7/2005 | Prokoski | |
| 7,431,700 B2 | 10/2008 | Aoki et al. | |
| 7,558,618 B1 | 7/2009 | Williams | |
| 8,149,273 B2 | 4/2012 | Liu et al. | |
| 8,754,772 B2 | 6/2014 | Horng et al. | |
| 8,792,969 B2 | 7/2014 | Bernal et al. | |
| 8,971,985 B2 | 3/2015 | Bernal et al. | |
| 9,226,691 B2 | 1/2016 | Bernal et al. | |
| 9,282,725 B2 | 3/2016 | Jensen-Jarolim et al. | |
| 9,301,710 B2 | 4/2016 | Mestha et al. | |
| 9,402,601 B1 | 8/2016 | Berger et al. | |
| 9,436,984 B2 | 9/2016 | Xu et al. | |
| 9,443,289 B2 | 9/2016 | Xu et al. | |
| 9,504,426 B2 | 11/2016 | Kyal et al. | |
| 9,662,022 B2 | 5/2017 | Kyal et al. | |
| 9,693,693 B2 | 7/2017 | Farag et al. | |
| 9,693,710 B2 | 7/2017 | Mestha et al. | |
| 9,697,599 B2 | 7/2017 | Prasad et al. | |
| 9,750,461 B1* | 9/2017 | Telfort ................ | A61B 5/7246 |
| 9,839,756 B2 | 12/2017 | Klasek | |
| 9,943,371 B2 | 4/2018 | Bresch et al. | |
| 10,278,585 B2 | 5/2019 | Ferguson et al. | |
| 10,376,147 B2 | 8/2019 | Wood et al. | |
| 10,398,353 B2 | 9/2019 | Addison et al. | |
| 10,523,852 B2 | 12/2019 | Tzvieli et al. | |
| 10,588,779 B2 | 3/2020 | Vorhees et al. | |
| 10,667,723 B2 | 6/2020 | Jacquel et al. | |
| 10,702,188 B2 | 7/2020 | Addison et al. | |
| 10,874,331 B2 | 12/2020 | Kaiser et al. | |
| 10,939,824 B2 | 3/2021 | Addison et al. | |
| 10,939,834 B2 | 3/2021 | Khwaja et al. | |
| 2004/0001633 A1 | 1/2004 | Caviedes | |
| 2004/0258285 A1* | 12/2004 | Hansen ................ | G06T 7/0012 |
| | | | 382/128 |
| 2005/0203348 A1 | 9/2005 | Shihadeh et al. | |
| 2007/0116328 A1* | 5/2007 | Sablak ............... | G06K 9/00362 |
| | | | 382/103 |
| 2008/0001735 A1 | 1/2008 | Tran | |
| 2008/0279420 A1 | 11/2008 | Masticola et al. | |
| 2008/0029583 A1 | 12/2008 | McCormick et al. | |
| 2008/0295837 A1 | 12/2008 | McCormick et al. | |
| 2009/0304280 A1* | 12/2009 | Aharoni ................. | G06T 7/162 |
| | | | 382/180 |
| 2010/0210924 A1 | 8/2010 | Parthasarathy et al. | |
| 2010/0236553 A1 | 9/2010 | Jafari et al. | |
| 2010/0249630 A1 | 9/2010 | Droitcour et al. | |
| 2010/0324437 A1 | 12/2010 | Freeman et al. | |
| 2011/0144517 A1 | 6/2011 | Cervantes | |
| 2011/0150274 A1* | 6/2011 | Patwardhan ......... | A61B 8/0891 |
| | | | 382/103 |
| 2012/0075464 A1 | 3/2012 | Derenne | |
| 2012/0065533 A1 | 5/2012 | Carrillo, Jr. et al. | |
| 2012/0243797 A1 | 9/2012 | Di Venuto Dayer et al. | |
| 2013/0271591 A1* | 10/2013 | Van Leest ................ | H04N 7/18 |
| | | | 348/77 |
| 2013/0272393 A1* | 10/2013 | Kirenko ............... | H04N 19/115 |
| | | | 375/240.08 |
| 2013/0275873 A1 | 10/2013 | Shaw et al. | |
| 2013/0324830 A1 | 12/2013 | Bernal et al. | |
| 2013/0324876 A1 | 12/2013 | Bernal et al. | |
| 2014/0023235 A1 | 1/2014 | Cennini et al. | |
| 2014/0052006 A1 | 2/2014 | Lee et al. | |
| 2014/0053840 A1 | 2/2014 | Liu | |
| 2014/0139405 A1 | 5/2014 | Ribble et al. | |
| 2014/0235976 A1 | 8/2014 | Bresch et al. | |
| 2014/0267718 A1 | 9/2014 | Govro et al. | |
| 2014/0272860 A1 | 9/2014 | Peterson et al. | |
| 2014/0275832 A1 | 9/2014 | Muehlsteff et al. | |
| 2014/0276104 A1* | 9/2014 | Tao ...................... | A61B 5/1128 |
| | | | 600/476 |
| 2014/0330336 A1 | 11/2014 | Errico et al. | |
| 2014/0334697 A1 | 11/2014 | Kersten et al. | |
| 2014/0358017 A1 | 12/2014 | Op Den Buijs et al. | |
| 2014/0378810 A1* | 12/2014 | Davis ................... | G16H 50/70 |
| | | | 600/407 |
| 2014/0379369 A1 | 12/2014 | Kokovidis et al. | |
| 2015/0003723 A1* | 1/2015 | Huang ................. | G06K 9/6269 |
| | | | 382/154 |
| 2015/0131880 A1* | 5/2015 | Wang ...................... | G06T 7/33 |
| | | | 382/131 |
| 2015/0157269 A1 | 6/2015 | Lisogurski et al. | |
| 2015/0223731 A1 | 8/2015 | Sahin | |
| 2015/0238150 A1 | 8/2015 | Subramaniam | |
| 2015/0265187 A1 | 9/2015 | Bernal et al. | |
| 2015/0282724 A1* | 10/2015 | McDuff ............. | A61B 5/02427 |
| | | | 600/479 |
| 2015/0301590 A1 | 10/2015 | Furst et al. | |
| 2015/0317814 A1* | 11/2015 | Johnston ................ | G06F 3/1256 |
| | | | 358/1.18 |
| 2016/0000335 A1* | 1/2016 | Khachaturian ........ | A61B 5/725 |
| | | | 600/474 |
| 2016/0049094 A1* | 2/2016 | Gupta ...................... | G09B 9/00 |
| | | | 434/185 |
| 2016/0082222 A1 | 3/2016 | Garcia et al. | |
| 2016/0143598 A1 | 5/2016 | Rusin et al. | |
| 2016/0151022 A1 | 6/2016 | Berlin et al. | |
| 2016/0156835 A1 | 6/2016 | Ogasawara et al. | |
| 2016/0174887 A1 | 6/2016 | Kirenko et al. | |
| 2016/0310084 A1* | 10/2016 | Banerjee ............. | G06T 7/0012 |
| 2016/0317041 A1 | 11/2016 | Porges et al. | |
| 2016/0345931 A1 | 12/2016 | Xu et al. | |
| 2016/0367186 A1 | 12/2016 | Freeman et al. | |
| 2017/0007342 A1 | 1/2017 | Kasai et al. | |
| 2017/0007795 A1 | 1/2017 | Pedro et al. | |
| 2017/0055877 A1 | 3/2017 | Niemeyer | |
| 2017/0065484 A1 | 3/2017 | Addison et al. | |
| 2017/0071516 A1 | 3/2017 | Bhagat et al. | |

(56) References Cited

U.S. PATENT DOCUMENTS

| | | | |
|---|---|---|---|
| 2017/0095215 | A1 | 4/2017 | Watson et al. |
| 2017/0095217 | A1 | 4/2017 | Hubert et al. |
| 2017/0119340 | A1 | 5/2017 | Nakai et al. |
| 2017/0147772 | A1 | 5/2017 | Meehan et al. |
| 2017/0164904 | A1 | 6/2017 | Kirenko |
| 2017/0172434 | A1 | 6/2017 | Amelard et al. |
| 2017/0238805 | A1 | 8/2017 | Addison et al. |
| 2017/0238842 | A1 | 8/2017 | Jacquel et al. |
| 2017/0311887 | A1 | 11/2017 | Leussler et al. |
| 2017/0319114 | A1 | 11/2017 | Kaestle |
| 2018/0042486 | A1* | 2/2018 | Yoshizawa ............ A61B 5/0077 |
| 2018/0042500 | A1 | 2/2018 | Liao et al. |
| 2018/0053392 | A1 | 2/2018 | White et al. |
| 2018/0104426 | A1 | 4/2018 | Oldfield et al. |
| 2018/0106897 | A1 | 4/2018 | Shouldice et al. |
| 2018/0169361 | A1 | 6/2018 | Dennis et al. |
| 2018/0217660 | A1 | 8/2018 | Dayal et al. |
| 2018/0228381 | A1 | 8/2018 | LeBoeuf et al. |
| 2018/0310844 | A1 | 11/2018 | Tezuka et al. |
| 2018/0325420 | A1 | 11/2018 | Gigi |
| 2018/0333050 | A1 | 11/2018 | Greiner et al. |
| 2019/0050985 | A1 | 2/2019 | Den Brinker et al. |
| 2019/0142274 | A1 | 5/2019 | Addison et al. |
| 2019/0199970 | A1 | 6/2019 | Greiner et al. |
| 2019/0209046 | A1 | 7/2019 | Addison et al. |
| 2019/0209083 | A1 | 7/2019 | Wu et al. |
| 2019/0307365 | A1 | 10/2019 | Addison et al. |
| 2019/0311101 | A1 | 10/2019 | Nienhouse |
| 2019/0343480 | A1 | 11/2019 | Shute et al. |
| 2019/0380599 | A1 | 12/2019 | Addison et al. |
| 2019/0380807 | A1 | 12/2019 | Addison et al. |
| 2020/0046302 | A1 | 2/2020 | Jacquel et al. |
| 2020/0187827 | A1 | 6/2020 | Addison et al. |
| 2020/0202154 | A1 | 6/2020 | Wang et al. |
| 2020/0205734 | A1 | 7/2020 | Mulligan et al. |
| 2020/0237225 | A1 | 7/2020 | Addison et al. |
| 2020/0242790 | A1 | 7/2020 | Addison et al. |
| 2020/0253560 | A1 | 8/2020 | De Haan |
| 2020/0289024 | A1 | 9/2020 | Addison et al. |
| 2020/0329976 | A1 | 10/2020 | Chen et al. |
| 2021/0068670 | A1 | 3/2021 | Redtel |
| 2021/0153746 | A1 | 5/2021 | Addison et al. |

FOREIGN PATENT DOCUMENTS

| | | |
|---|---|---|
| CN | 112233813 A | 1/2021 |
| DE | 19741982 A1 | 10/1998 |
| EP | 2428162 A1 | 3/2012 |
| EP | 2793189 A2 | 10/2014 |
| EP | 3207862 A1 | 8/2017 |
| EP | 3207863 A1 | 8/2017 |
| EP | 3384827 A1 | 10/2018 |
| EP | 2772828 B1 | 1/2019 |
| JP | 2009544080 A | 12/2009 |
| JP | 2011130996 A | 7/2011 |
| KR | 101644843 B1 | 8/2016 |
| WO | 2004100067 A2 | 11/2004 |
| WO | 2010034107 A1 | 4/2010 |
| WO | 2010036653 A1 | 4/2010 |
| WO | 2015059700 A1 | 4/2015 |
| WO | 2015078735 A1 | 6/2015 |
| WO | 2015110859 A1 | 7/2015 |
| WO | 2016065411 A1 | 5/2016 |
| WO | 2016178141 A1 | 11/2016 |
| WO | 2016209491 A1 | 12/2016 |
| WO | 2017060463 A1 | 4/2017 |
| WO | 2017089139 A1 | 6/2017 |
| WO | 2017144934 A1 | 8/2017 |
| WO | 2018042376 A1 | 3/2018 |
| WO | 2019094893 A1 | 5/2019 |
| WO | 2019135877 A1 | 7/2019 |
| WO | 2019240991 A1 | 12/2019 |
| WO | 2020033613 A1 | 2/2020 |
| WO | 2021044240 A1 | 3/2021 |

OTHER PUBLICATIONS

International Search Report and Written Opinion for International Application No. PCT/US2018/065492, dated Mar. 8, 2019, 12 pages.

International Search Report and Written Opinion for International Application No. PCT/US19/035433, dated Nov. 11, 2019, 17 pages.

Feng, Litong et al., "Dynamic ROI based on K-means for remote photoplethysmography", IEEE International Conference on Acoustics, Speech and Signal Processing (ICASSP), Apr. 2015, p. 1310-1314. (Year: 2015).

European Search Report; European Patent Application No. 17156334.9; Applicant: Covidien LP; dated Jul. 13, 2017, 10 pgs.

Lai, C. J. et al. "Heated humidified high-flow nasal oxygen prevents intraoperative body temperature decrease in non-intubated thoracoscopy." Journal of Anesthesia. Oct. 15, 2018. 8 pages.

Pereira, C. et al. "Noncontact Monitoring of Respiratory Rate in Newborn Infants Using Thermal Imaging." IEEE Transactions on Biomedical Engineering. Aug. 23, 2018. 10 pages.

Yu et al. "Motion-compensated noncontact imaging photoplethysmography to monitor cardiorespiratory status during exercise," Journal of Biomedical Optics, vol. 16, No. 7, Jan. 1, 2011, 10 pages.

Ni et al. "RGBD-Camera Based Get-Up Event Detection for Hos-pital Fall Prevention." Acoustics, Speech and Signal Processing (ICASSP). 2012 IEEE International Conf., Mar. 2012: pp. 1405-1408.

European Search Report; European Patent Application No. 17156337.2; Applicant: Covidien LP; dated Jul. 13, 2017, 10 pgs.

Goldman, L. J., "Nasal airflow and thoracoabdominal motion in children using infrared thermographic video processing,", Pediatric Pulmonology, vol. 47, No. 5, pp. 476-486, 2012.

Wang, W. et al., "Exploiting spatial redundancy of image sensor for motion robust rPPG." IEEE Transactions on Biomedical Engineering, vol. 62, No. 2, pp. 415-425, 2015.

Bruser, C. et al., "Adaptive Beat-to-Beat Heart Rate Estimation in Ballistocardiograms," IEEE Transactions Information Technology in Biomedicine, vol. 15, No. 5, Sep. 2011, pp. 778-786.

Rubinstein, M., "Analysis and Visualization of Temporal Variations in Video", Department of Electrical Engineering and Computer Science, Massachusetts Institute of Technology, Feb. 2014, 118 pages.

Wadhwa, N. et al., "Phase-Based Video Motion Processing," MIT Computer Science and Artificial Intelligence Lab, Jul. 2013, 9 pages.

Wadhwa, N. et al., "Riesz pyramids for fast phase-based video magnification." in Proc. ofIEEE International Conference on Computational Photography (ICCP), Santa Clara, CA, pp. 1-10, 2014.

Klaessens J. H. G. M. et al., "Non-invasive skin oxygenation imaging using a multi-spectral camera system: Effectiveness of various concentration algorithms applied on human skin," Proc. of SPIE vol. 7174 717408-1, 2009, 14 pages.

Addison, P. S. et al., "Video-based Heart Rate Monitoring across a Range of Skin Pigmentations during an Acute Hypoxic Challenge," J Clin Monit Comput, Nov. 9, 2017, 10 pages.

Liu, C. et al., "Motion magnification" ACM Transactions on Graphics (TOG), vol. 24, No. 3, pp. 519-526, 2005.

Abbas A. K. et al., "Neonatal non-contact respiratory monitoring based on real-time infrared thermography," Biomed. Eng. Online, vol. 10, No. 93, 2011, 17 pages.

Teichmann, D. et al., "Non-contact monitoring techniques—Principles and applications," in Proc. of IEEE International Conference of the Engineering in Medicine and Biology Society (EMBC), San Diego, CA, 2012, 4 pages.

Li et al., "A Non-Contact Vision-Based System for Respiratory Rate Estimation", 978-I-4244-7929-0/14, 2014, 4 pages.

Kortelainen, J. et al., "Sleep staging based on signals acquired through bed sensor," IEEE Transactions on Information Technology in Biomedicine, vol. 14, No. 3, pp. 776-785, May 2010.

Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-522.

(56) References Cited

OTHER PUBLICATIONS

Mestha, L.K. et al., "Towards Continuous Monitoring of Pulse Rate in Neonatal Intensive Care Unit with a Webcam" in Proc. of 36th Annual Int. Conf. of the IEEE Engineering in Medicine and Biology Society, Chicago, Il pp. 1-5, 2014.

Fei J. et al., "Thermistor at a distance: unobtrusive measurement of breathing," IEEE Transactions on Biomedical Engineering, vol. 57, No. 4, pp. 988-998, 2010.

Han, J. et al., "Visible and infrared image registration in man-made environments employing hybrid visual features," Pattern Recognition Letters, vol. 34, No. 1, pp. 42-51, 2013.

Nu, H.Y. et al., "Eulerian video magnification for revealing subtle changes in the world," ACM Transactions on Graphics (TOG), vol. 31, No. 4, pp. 651-658, 2012.

Bhattacharya, S. et al., "Unsupervised learning using Gaussian Mixture Copula models," 21st International Conference on Computational Statistics (COMPSTAT 2014), Geneva, Switzerland, 2014, 8 pages.

Huddar, V. et al., "Predicting Postoperative Acute Respiratory Failure in Critical Care using Nursing Notes and Physiological Signals," 36th Annual International Conference of IEEE Engineering in Medicine and Biology Society (IEEE EMBC2014), Chicago, USA, 2014, pp. 2702-2705.

Bhattacharya, S. et al., "A Novel Classification Method for Predicting Acute Hypotensive Episodes in Critical Care," 5th ACM Conference on Bioinformatics, Computational Biology and Health Informatics (ACM-BCB 2014), Newport Beach, USA, 2014, 10 pages.

Zhou, J. et al., "Maximum parsimony analysis of gene copy number changes in tumor phylogenetics," 15th International Workshop on Algorithms in Bioinformatics WABI 2015, Atlanta, USA, 13 pages.

Shrivastava, H. et al., "Classification with Imbalance: A Similarity-based Method for Predicting Respiratory Failure," 2015 IEEE International Conference on Bio informatics and Biomedicine (IEEE BIBM2015), Washington DC, USA, 8 pages.

Rajan, V. et al., "Clinical Decision Support for Stroke using MultiviewLearning based Models for NIHSS Scores," PAKDD 2016 Workshop: Predictive Analytics in Critical Care (PACC), Auckland, New Zealand, 10 pages.

Rajan, V. et al., "Dependency Clustering of Mixed Data with Gaussian Mixture Copulas," 25th International Joint Conference on Artificial Intelligence IJCAI 2016, New York, USA, 7 pages.

Sengupta, A. et al., "A Statistical Model for Stroke Outcome Prediction and Treatment Planning," 38th Annual International Conference of the IEEE Engineering in Medicine and Biology (Society IEEE EMBC 2016), Orlando, USA, 2016, 4 pages.

Reisner, A. et al., "Utility of the Photoplethysmogram in Circulatory Monitoring". American Society of Anesthesiologist, May 2008, pp. 950-958.

Tamura et al., "Wearable Photoplethysmographic Sensors—Past & Present," Electronics, 2014, pp. 282-302.

Poh et al., "Non-contact, automated cardiac pulse measurements using video imaging and blind source separation," Opt. Express 18,10762-10774 (2010), 14 pages.

Kumar, M. et al., "Distance PPG: Robust non-contact vital signs monitoring using a camera," Biomedical optics express 2015, 24 pages.

Colantonio, S. "A smart mirror to promote a healthy lifestyle," Biosystems Engineering, vol. 138, Oct. 2015, pp. 33-43, Innovations in Medicine and Healthcare.

Scalise, Lorenzo, et al., "Heart rate measurement in neonatal patients using a webcamera.", 978-I-4673-0882-3/12, IEEE, 2012, 4 pages.

Javadi M. et al., "Diagnosing Pneumonia in Rural Thailand: Digital Cameras versus Film Digitizers for Chest Radiograph Teleradiology," International Journal of Infectious Disease, Mar. 2006; 10(2), pp. 129-135.

Liu H. et al., "A Novel Method Based on Two Cameras for Accurate Estimation of Arterial Oxygen Saturation,". BioMedical Engineering OnLine, 2015, 17 pages.

George et al., "Respiratory Rate Measurement From PPG Signal Using Smart Fusion Technique," International Conference on Engineering Trends and Science & Humanities (ICETSH-2015), 5 pages, 2015.

Addison, Paul S. PhD, "A Review of Signal Processing Used in the Implementation of the Pulse Oximetry Phtoplethysmographic Fluid Responsiveness Parameter", International Anesthesia Research Society, Dec. 2014, vol. 119, No. 6, pp. 1293-1306.

McDuff, Daniel J., et al., "A Survey of Remote Optical Photoplethysmographic Imaging Methods", 978-1-4244-9270-I/I6, IEEE, 2015, pp. 6398-6404.

Poh, et al., "Advancements in Noncontact, Multiparameter Physiological Measurements Using a Webcam", IEEE Transactions on Biomedical Engineering, vol. 58, No. 1, Jan. 2011, 5 pages.

Addison, Paul S., et al., "Developing an algorithm for pulse oximetry derived respiratory rate (RRoxi): a healthy volunteer study", J Clin Monit Comput (2012) 26, pp. 45-51.

Bickler, Philip E. et al., "Factors Affecting the Performance of 5 Cerebral Oximeters During Hypoxia in Healthy Volunteers", Society for Technology in Anesthesia, Oct. 2013, vol. 117, No. 4, pp. 813-823.

Verkruysse, Wim, et al., "Calibration of Contactless Pulse Oximetry", Anesthesia & Analgesia, Jan. 2017, vol. 124, No. 1, pp. 136-145.

Cennini, Giovanni, et al., "Heart rate monitoring via remote phtoplethysmography with motion artifacts reduction", Optics Express, Mar. 1, 2010, vol. 18, No. 5, pp. 4867-4875.

Lv, et al., "Class Energy Image Analysis for Video Sensor-Based Gait Recognition: A Review", Sensors 2015, 15, pp. 932-964.

Villarroel, Mauricio, et al., "Continuous non-contact vital sign monitoring in neonatal intensive care unit", Healthcare Technology Letters, 2014, vol. 1, Issue. 3, pp. 87-91.

Bousefsaf, Frederic, et al., "Continuous wavelet filtering on webcam photoplethysmographic signals to remotely assess the instantaneous heart rate", Biomedical Signal Processing and Control 8, 2013, pp. 568-574.

BSI Standards Publication, "Medical electrical equipment, Part 2-61: Particular requirements for basic safety and essential performance of pulse oximeter equipment", BS EN ISO 80601-2-61:2011, 98 pages.

Jopling, Michael W., et al., "Issues in the Laboratory Evaluation of Pulse Oximeter Performance", Anesth. Analg. 2002; 94, pp. S62-S68.

Kong, Lingqin, et al., "Non-contact detection of oxygen saturation based on visible light imaging device using ambient light", Optics Express, Jul. 29, 2013, vol. 21, No. 15, pp. 17464-17471.

Aarts, Lonneke A.M., et al., "Non-contact heart rate monitoring utilizing camera photoplethysmography in the neonatal intensive care unit—A pilot study", Early Human Development 89, 2013, pp. 943-948.

Sun, Yu, et al., "Noncontact imaging phtoplethysmography to effectively access pulse rate variability", Journal of Biomedical Optics, Jun. 2013, vol. 18(6), 10 pages.

Guazzi, Alessandro R., et al., "Non-contact measurement of oxygen saturation with an RGB camera", Biomedical Optics Express, Sep. 1, 2015, vol. 6, No. 9, pp. 3320-3338.

Shao, Dangdang, et al., "Noncontact Monitoring Breathing Pattern, Exhalation Flow Rate and Pulse Transit Time", IEEE Transactions on Biomedical Engineering, vol. 61, No. 11, Nov. 2014, pp. 2760-2767.

Tarassenko, L., et al., "Non-contact video-based vital sign monitoring using ambient light and auto-regressive models", Institute of Physics and Engineering in Medicine, 2014, pp. 807-831.

Shah, Nitin, et al., "Performance of three new-generation pulse oximeters during motion and low perfusion in volunteers". Journal of Clinical Anesthesia, 2012, 24, pp. 385-391.

Kwon, Sungjun, et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177.

Addison,Paul S., et al., "Pulse oximetry-derived respiratory rate in general care floor patients", J Clin Monit Comput, 2015, 29, pp. 113-120.

(56) References Cited

OTHER PUBLICATIONS

Rougier, Caroline, et al., "Robust Video Surveillance for Fall Detection Based on Human Shape Deformation", IEEE Transactions on Circuits and Systems for Video Technology, vol. 21, No. 5, May 2011, pp. 611-622.
Cooley et al. "An Algorithm for the Machine Calculation of Complex Fourier Series," Aug. 17, 1964, pp. 297-301. International Search Report and Written Opinion for International Application No. PCT/US2018/065492, dated Mar. 8, 2019, 12 pages.
Amelard, et al., "Non-contact transmittance photoplethysmographic imaging (PPGI) for long-distance cardiovascular monitoring," ResearchGate, Mar. 23, 2015, pp. 1-13, XP055542534.
Nisar, et al. "Contactless heart rate monitor for multiple persons in a video", IEEE International Conference on Consumer Electronics-Taiwan (ICCE-TW), May 27, 2016, pp. 1-2, XP032931229.
International Search Report and Written Opinion for International Application No. PCT/US2018/060648, dated Jan. 28, 2019, 13 pages.
International Application No. PCT/US2019/035433 Invitation to Pay Additional Fees and Partial International Search Report dated Sep. 13, 2019, 13 pages.
International Application No. PCT/US2019/045600 International Search Report and Written Opinion dated Oct. 23, 2019, 14 pages.
Nguyen, et al., "3D shape, deformation and vibration measurements using infrared Kinect sensors and digital image correlation", Applied Optics, vol. 56, No. 32, Nov. 8, 2017, 8 pages.
Povsi, et al., "Real-Time 3D visualization of the thoraco-abdominal surface during breathing with body movement and deformation extraction", Physiological Measurement, vol. 36, No. 7, May 28, 2015, pp. 1497-1516.
Prochazka et al., "Microsoft Kinect Visual and Depth Sensors for Breathing and Heart Rate Analysis", Sensors, vol. 16, No. 7, Jun. 28, 2016, 11 pages.
Schaerer, et al., "Multi-dimensional respiratory motion tracking from markerless optical surface imaging based on deformable mesh registration", Physics in Medicine and Biology, vol. 57, No. 2, Dec. 14, 2011, 18 pages.
Zaunseder, et al. "Spatio-temporal analysis of blood perfusion by imaging photoplethysmography," Progress in Biomedical Optics and Imaging, SPIE—International Society for Optical Engineering, vol. 10501, Feb. 20, 2018, 15 pages.
Barone, et al., "Computer-aided modelling of three-dimensional maxillofacial tissues through multi-modal imaging", Journal of Engineering in Medicine, Part H. vol. 227, No. 2, Feb. 1, 2013, pp. 89-104.
Barone, et al., "Creation of 3D Multi-body Orthodontic Models by Using Independent Imaging Sensors", Senros MDPI AG Switzerland, vol. 13, No. 2, Jan. 1, 2013, pp. 2033-2050.
Armanian, A. M., "Caffeine administration to prevent apnea in very premature infants", Pediatrics & Neonatology, 57(5), 2016, pp. 408-412, 5 pages.
Di Fiore, J.M., et al., "Intermittent hypoxemia and oxidative stress in preterm infants", Respiratory Physiology & Neurobiology, No. 266, 2019, pp. 121-129, 25 pages.
Grimm, T., et al., "Sleep position classification from a depth camera using bed aligned maps", 23rd International Conference on Pattern Recognition (ICPR), Dec. 2016, pp. 319-324, 6 pages.
Liu, S., et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.
Wulbrand, H., et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.
Amazon, "Dockem Koala Tablet Wall Mount Dock for iPad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.
Gsmarena, "Apple iPad Pro 11 (2018)", https://www.gsmarena.com/apple_ipad_pro_11_(2018)-9386.pjp, viewed on Nov. 16, 2021, Nov. 16, 2021, 1 page.

\* cited by examiner

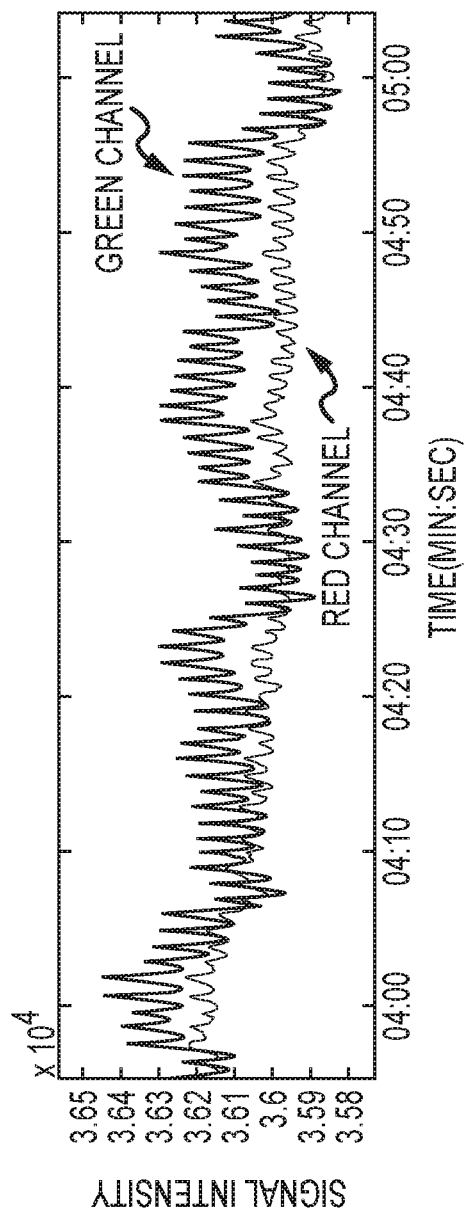
FIG. 8A
FIG. 8B

SYSTEMS AND METHODS FOR VIDEO-BASED MONITORING OF VITAL SIGNS

RELATED APPLICATIONS

This application claims priority to and the benefit of U.S. Provisional Application No. 62/297,682 (filed Feb. 19, 2016); U.S. Provisional Application No. 62/335,862 (filed May 13, 2016); and U.S. Provisional Application No. 62/399,741 (filed Sep. 26, 2016), the contents of which are incorporated herein by reference in their entirety.

BACKGROUND

Many conventional medical monitors require attachment of a sensor to a patient in order to detect physiologic signals from the patient and transmit detected signals through a cable to the monitor. These monitors process the received signals and determine vital signs such as the patient's pulse rate, respiration rate, and arterial oxygen saturation. An example of a prior art monitoring system 100 is shown in FIG. 1. The system 100 includes a monitor 110 and a sensor 112 connected to the monitor 110 by a cable 114. In the example of FIG. 1, the monitor 110 is a pulse oximeter, and the sensor 112 is a finger sensor including two light emitters and a photodetector. The sensor 112 emits light into the patient's finger, detects light transmitted through the patient's finger, and transmits the detected light signal through the cable 114 to the monitor 110. The monitor 110 includes a processor that processes the signal, determines vital signs (including pulse rate, respiration rate, and arterial oxygen saturation), and displays them on an integrated display 116.

Other monitoring systems include other types of monitors and sensors, such as electroencephalogram (EEG) sensors, blood pressure cuffs, temperature probes, and others.

Many of these conventional monitors require some type of cable or wire, such as cable 114 in FIG. 1, physically connecting the patient to the monitor. As a result, the patient is effectively tethered to the monitor, which can limit the patient's movement around a hospital room, restrict even simple activities such as writing or eating, and prevent easy transfer of the patient to different locations in the hospital without either disconnecting and connecting new monitors, or moving the monitor with the patient.

Some wireless, wearable sensors have been developed, such as wireless EEG patches and wireless pulse oximetry sensors. Although these sensors improve patient mobility, they introduce new problems such as battery consumption, infection risk from re-use on sequential patients, high cost, and bulky designs that detract from patient compliance and comfort.

Video-based monitoring is a new field of patient monitoring that uses a remote video camera to detect physical attributes of the patient. This type of monitoring may also be called "non-contact" monitoring in reference to the remote video sensor, which does not contact the patient. The remainder of this disclosure offers solutions and improvements in this new field.

BRIEF DESCRIPTION OF THE DRAWINGS

FIG. 8A is a chart of intensity signals acquired by flood fill filtering of a video signal, according to an embodiment of the invention.

FIG. 8B zooms in on a segment of FIG. 8A.

SUMMARY

Figure 1:
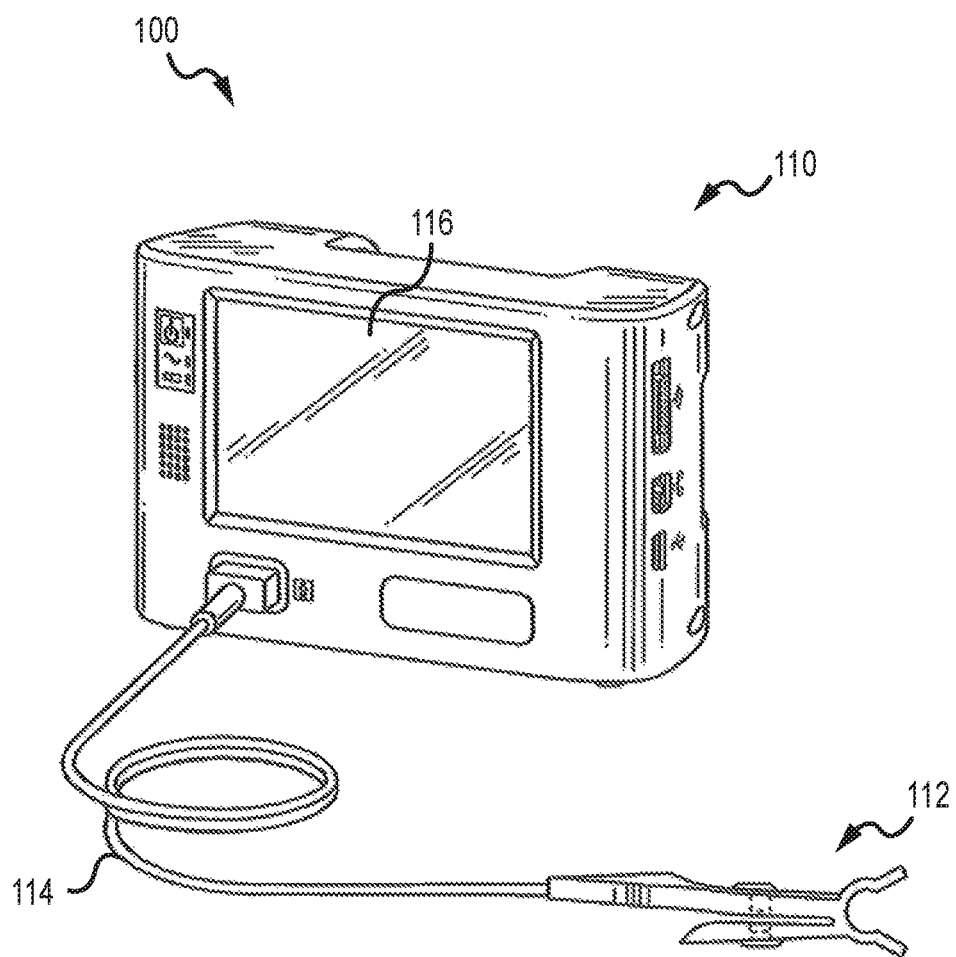
FIG. 1 is a perspective view of a pulse oximetry monitor and sensor according to the prior art.

In an embodiment, a video-based method of measuring a patient's vital sign includes receiving, from a video camera, a video signal having a field of view exposed to a patient; displaying, on a display screen, the video signal, or a portion of the video signal, to a user; receiving, in conjunction with the display screen, a user input that locates, within the video signal, an area of the patient; establishing, with a processor, a region of interest in the located area; extracting an intensity signal from the region of interest; measuring a vital sign from the intensity signal; and outputting the vital sign for further processing or display.

In an embodiment, the user input comprises a touch on the display screen at the patient's forehead. In an embodiment, the user input comprises a gesture on the display screen around the patient's face or forehead. In an embodiment, the user input comprises a touch on the display screen at the patient's eye or nose, and establishing the region of interest comprises inferring a forehead location from the touch input, and the region of interest comprises a portion of the forehead.

In an embodiment, prior to receiving the user input, the user is prompted to locate the area of the patient. In an embodiment, prior to receiving the user input, the user is prompted to touch the face or forehead of the patient.

In an embodiment, the user input comprises first and second touches on the display screen, the touches indicating first and second opposite ends of the patient's face or forehead.

In an embodiment, the area comprises a hand of the patient. In an embodiment, the area comprises a face of the patient.

In an embodiment, the user input comprises a touch on the display screen identifying a first seed point on exposed skin of the patient, and establishing a region of interest comprises flood filling a first contiguous region from the first seed point.

In an embodiment, the method includes recognizing, with a processor, a facial feature of the patient, and prompting the user to confirm the recognized facial feature, and the user input comprises a touch confirmation. In an embodiment, establishing a region of interest comprises locating a first seed point relative to the recognized facial feature and flood filling a first contiguous region from the first seed point.

In an embodiment, the user input comprises a gesture around the area, and establishing a region of interest comprises flood filling a first contiguous region in the area, and discarding a portion of the first contiguous region to create the region of interest. In an embodiment, the user input comprises a gesture around the area, and establishing a region of interest comprises selecting a first seed point in the area, adjusting a skin tone filter based on properties of the first seed point, skin tone filtering with the skin tone filter to identify candidate skin pixels, and extracting the intensity signal from the candidate skin pixels within the region of interest.

In an embodiment, the method includes receiving, at the display screen, a second user input confirming the region of interest. In an embodiment, the method includes, prior to receiving the user input, prompting the user for the user input, in response to a determination of low or no confidence in an automated facial recognition.

In an embodiment, a method for video-based monitoring of a patient's vital sign includes receiving, from a video camera, a video signal encompassing exposed skin of a patient; identifying, using a processor, first and second regions of interest on the patient's exposed skin; filtering, using the processor, the video signal with a skin tone filter to identify candidate skin pixels within each region of interest; extracting a first intensity signal from the candidate skin pixels within the first region of interest; extracting a second intensity signal from the candidate skin pixels within the second region of interest; selecting either the first intensity signal, the second intensity signal, or a combination of the first and second intensity signals; measuring a vital sign from the selected intensity signal; and outputting the vital sign for further processing or display.

In an embodiment, the method also includes identifying a seed point on the patient, flooding a contiguous region from the seed point, and determining, from the flooded contiguous region, a range of color values for the skin tone filter. In an embodiment, the method also includes identifying an anatomical feature on the patient, and assigning the seed point in spatial relation to the anatomical feature. In an embodiment, the anatomical feature comprises a forehead.

In an embodiment, the method also includes dynamically updating the flooded contiguous region and the range of color values for the skin tone filter over time, and filtering the video signal with the updated range of color values. In an embodiment, determining the range of values comprises identifying, during a calibration time period, intensity values from pixels in the flooded contiguous region, and setting the range around the identified intensity values.

In an embodiment, the method also includes setting a range of color values for the skin tone filter, and wherein filtering the video signal with the skin tone filter to identify candidate skin pixels within each region of interest comprises identifying as the candidate skin pixels those pixels that fall within the range of color values. In an embodiment, the range of color values is selected from a predefined set of suggested ranges. In an embodiment, the method also includes receiving, in conjunction with a display screen, a user input identifying, within the video signal, a location on the patient, determining exhibited color values exhibited by pixels at the location, and setting the range of color values based on the exhibited color values.

In an embodiment, the method also includes generating a first histogram from the first intensity signal and a second histogram from the second intensity signal, and identifying the first and second intensity signals as uni-modal, bi-modal, or multi-modal based on the respective histograms. In an embodiment, the first intensity signal exhibits a uni-modal intensity distribution, and wherein selecting comprises selecting the first intensity signal. In an embodiment, both the first and second intensity signals exhibit a uni-modal intensity distribution, and selecting an intensity signal comprises selecting the signal extracted from the region with the largest size.

In an embodiment, the first region is larger than the second region, and wherein selecting comprises selecting the first intensity signal. In an embodiment, the first intensity signal has a higher signal to noise ratio than the second intensity signal, and selecting comprises selecting the first intensity signal. In an embodiment, an intensity signal that presents a bi-modal intensity distribution is discarded or down-weighted.

In an embodiment, the candidate skin pixels are non-contiguous. In an embodiment, the first region of interest comprises a forehead region, and the second region of interest comprises a cheek region. In an embodiment, the first region of interest comprises a first forehead region, and the second region of interest comprises a second forehead region that is smaller than the first forehead region. In an embodiment, the first and second regions of interest are non-overlapping.

In an embodiment, a method for video-based monitoring of a patient's vital signs includes receiving, from a video camera, a video signal encompassing exposed skin of a patient; filtering, using a processor, the video signal with a skin tone filter to identify candidate skin pixels; identifying, using the processor, a region of interest that encompasses at least some of the candidate skin pixels and that presents a unimodal intensity distribution; extracting an intensity signal from the region of interest; measuring a vital sign from the intensity signal; and outputting the vital sign for further processing or display.

DETAILED DESCRIPTION

The present invention relates to the field of medical monitoring, and in particular non-contact, video-based monitoring of pulse rate, respiration rate, motion, activity, and oxygen saturation. Systems and methods are described for receiving a video signal in view of a patient, identifying a physiologically relevant area within the video image (such as a patient's forehead or chest), extracting a light intensity signal from the relevant area, and measuring a vital sign from the extracted intensity signal. The video signal is detected by a camera that views but does not contact the patient. With appropriate selection and filtering of the video signal detected by the camera, the physiologic contribution to the detected signal can be isolated and measured, producing a useful vital sign measurement without placing a detector in physical contact with the patient. This approach has the potential to improve patient mobility and comfort, along with many other potential advantages discussed below.

As used herein, the term "non-contact" refers to monitors whose measuring device (such as a detector) is not in physical contact with the patient. Examples include cameras, accelerometers mounted on a patient bed without contacting the patient, radar systems viewing the patient, and others. "Video-based" monitoring is a sub-set of non-contact monitoring, employing one or more cameras as the measuring device. In an embodiment, the camera produces an image stack, which is a time-based sequence of images of the camera's field of view. The camera may be considered a "video" camera if the frame rate is fast enough to create a moving, temporal image signal.

Remote sensing of a patient in a video-based monitoring system presents several new challenges. One challenge is presented by motion. The problem can be illustrated with the example of pulse oximetry. Conventional pulse oximetry sensors include two light emitters and a photodetector. The sensor is placed in contact with the patient, such as by clipping or adhering the sensor around a finger, toe, or ear of a patient. The sensor's emitters emit light of two particular wavelengths into the patient's tissue, and the photodetector detects the light after it is reflected or transmitted through the tissue. The detected light signal, called a photoplethysmogram (PPG), modulates with the patient's heartbeat, as each arterial pulse passes through the monitored tissue and affects the amount of light absorbed or scattered. Movement of the patient can interfere with this contact-based oximetry, introducing noise into the PPG signal due to compression of the monitored tissue, disrupted coupling of the sensor to the finger, pooling or movement of blood, exposure to ambient light, and other factors. Modern pulse oximeters employ filtering algorithms to remove noise introduced by motion and to continue to monitor the pulsatile arterial signal.

However, movement in non-contact pulse oximetry creates different complications, due to the extent of movement possible between the patient and the camera, which acts as the detector. Because the camera is remote from the patient, the patient may move toward or away from the camera, creating a moving frame of reference, or may rotate with respect to the camera, effectively morphing the region that is being monitored. Thus, the monitored tissue can change morphology within the image frame over time. This freedom of motion of the monitored tissue with respect to the detector introduces new types of motion noise into the video-based signals.

Another challenge is the contribution of ambient light. In this context, "ambient light" means surrounding light not emitted by components of the medical monitor. In contact-based pulse oximetry, the desired light signal is the reflected and/or transmitted light from the light emitters on the sensor, and ambient light is entirely noise. The ambient light can be filtered, removed, or avoided in order to focus on the desired signal. In contact-based pulse oximetry, contact-based sensors can be mechanically shielded from ambient light, and direct contact between the sensor and the patient also blocks much of the ambient light from reaching the detector. By contrast, in non-contact pulse oximetry, the desired physiologic signal is generated or carried by the ambient light source; thus, the ambient light cannot be entirely filtered, removed, or avoided as noise. Changes in lighting within the room, including overhead lighting, sunlight, television screens, variations in reflected light, and passing shadows from moving objects all contribute to the light signal that reaches the camera. Even subtle motions outside the field of view of the camera can reflect light onto the patient being monitored. Thus new filtering techniques are needed to isolate the physiologic signal from this combined ambient light signal.

If these challenges are addressed, non-contact monitoring such as video-based monitoring can deliver significant benefits. Some video-based monitoring can reduce cost and waste by reducing usage of disposable contact sensors, replacing them with reusable camera systems. Video monitoring may also reduce the spread of infection, by reducing physical contact between caregivers and patients (otherwise incurred when the caregiver places, adjusts, or removes the contact sensor on the patient). Some remote video cameras may improve patient mobility and comfort, by freeing patients from wired tethers or bulky wearable sensors. This untethering may benefit patients who need exercise and movement. In some cases, these systems can also save time for caregivers, who no longer need to reposition, clean, inspect, or replace contact sensors. Another benefit comes from the lack of sensor-off alarms or disruptions. A traditional contact-based system can lose the physiologic signal when the contact sensor moves or shifts on the patient, triggering alarms that are not actually due to a change in physiology. In an embodiment, a video-based system does not drop readings due to sensors moving or falling off the patient (sensor off) or becoming disconnected from the monitor (sensor disconnect), and thus can reduce nuisance alarms. In an embodiment, a video-based monitor, such as a pulse oximeter, operates without sensor-off or sensor-disconnect alarms. For example, a video-based monitor can trigger an alarm based on stored alarm conditions, where the stored alarm conditions omit a sensor-off or sensor-disconnect alarm.

Figure 2A:
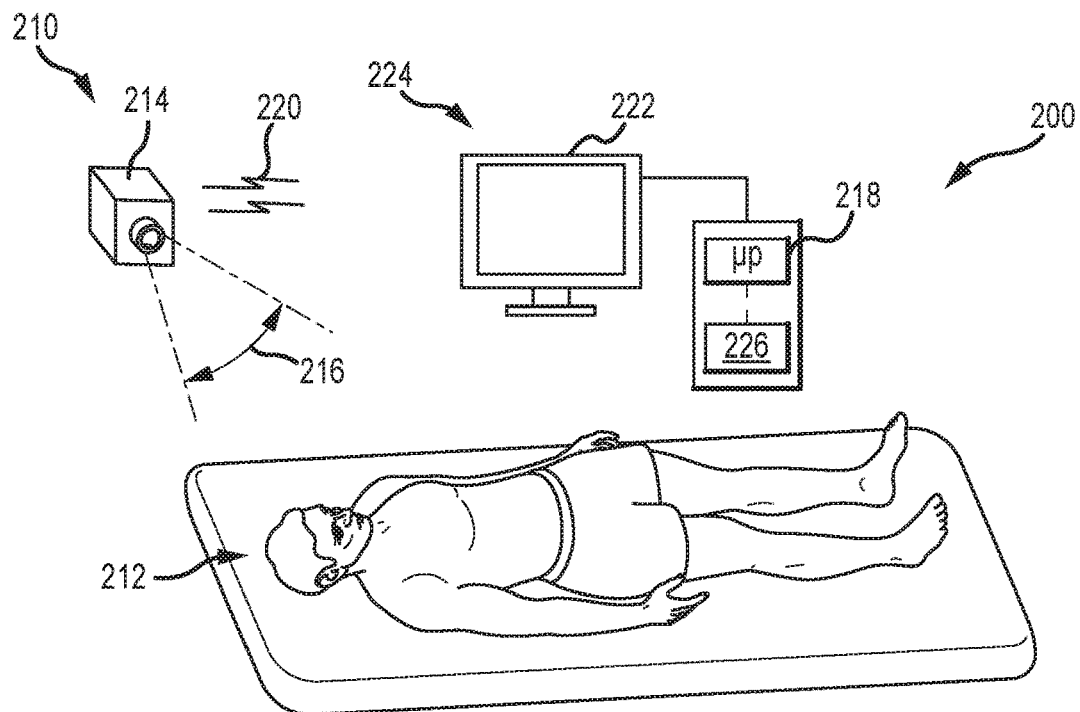
FIG. 2A is schematic view of a video-based patient monitoring system according to an embodiment of the invention.

Various embodiments of the present invention are described below, to address some of these challenges. FIG. 2A shows a video-based remote monitoring system 200 and a patient 212, according to an embodiment. The system 200 includes a non-contact detector 210 placed remote from the patient 212. In this embodiment, the detector 210 includes a camera 214, such as a video camera. The camera 214 is remote from the patient, in that it is spaced apart from and does not contact the patient. The camera includes a detector exposed to a field of view 216 that encompasses at least a portion of the patient 212. In some embodiments, the field of view 216 encompasses exposed skin of the patient, in order to detect physiologic signals visible from the skin, such as arterial oxygen saturation (SpO2 or $S_{vid}O2$). The camera generates a sequence of images over time. A measure of the amount, color, or brightness of light within all or a portion of the image over time is referred to as a light intensity signal. In an embodiment, each image includes a two-dimensional array or grid of pixels, and each pixel includes three color components—for example, red, green, and blue. A measure of one or more color components of one or more pixels over time is referred to as a "pixel signal," which is a type of light intensity signal. The camera operates at a frame rate, which is the number of image frames taken per second (or other time period). Example frame rates include 20, 30, 40, 50, or 60 frames per second, greater than 60 frames per second, or other values between those. Frame rates of 20-30 frames per second produce useful signals, though frame rates above 50 or 60 frames per second are helpful in avoiding aliasing with light flicker (for artificial lights having frequencies around 50 or 60 Hz).

The detected images are sent to a monitor 224, which may be integrated with the camera 214 or separate from it and coupled via wired or wireless communication with the camera (such as wireless communication 220 shown in FIG. 2A). The monitor 224 includes a processor 218, a display 222, and hardware memory 226 for storing software and computer instructions. Sequential image frames of the patient are recorded by the video camera 214 and sent to the processor 218 for analysis. The display 222 may be remote from the monitor 224, such as a video screen positioned separately from the processor and memory.

Figure 2B:
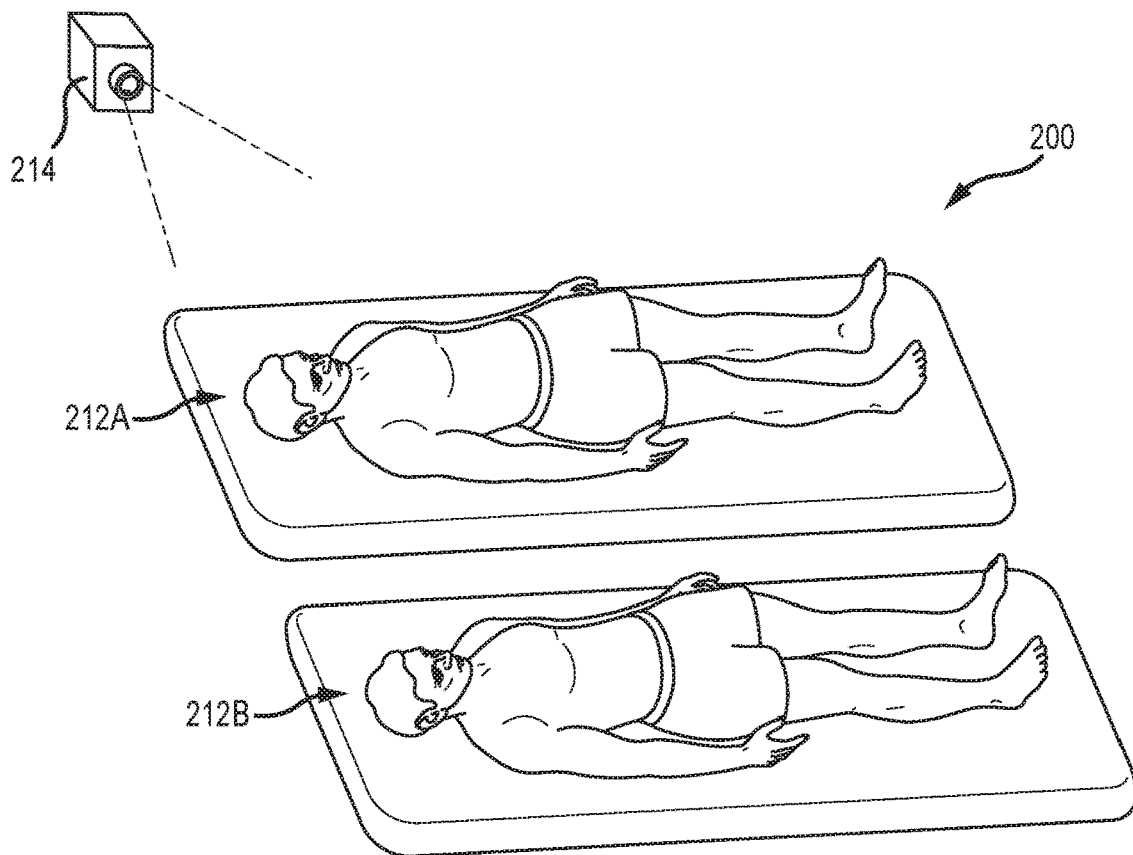
FIG. 2B is schematic view of a video-based patient monitoring system monitoring multiple patients according to an embodiment of the invention.

FIG. 2B shows the system 200 being implemented to monitor multiple patients, such as patients 212A and 212B. Because the detector 214 in the system is non-contact, it can be used to monitor more than one patient at the same time. A method for this implementation will be described in further detail below.

Figure 3A:
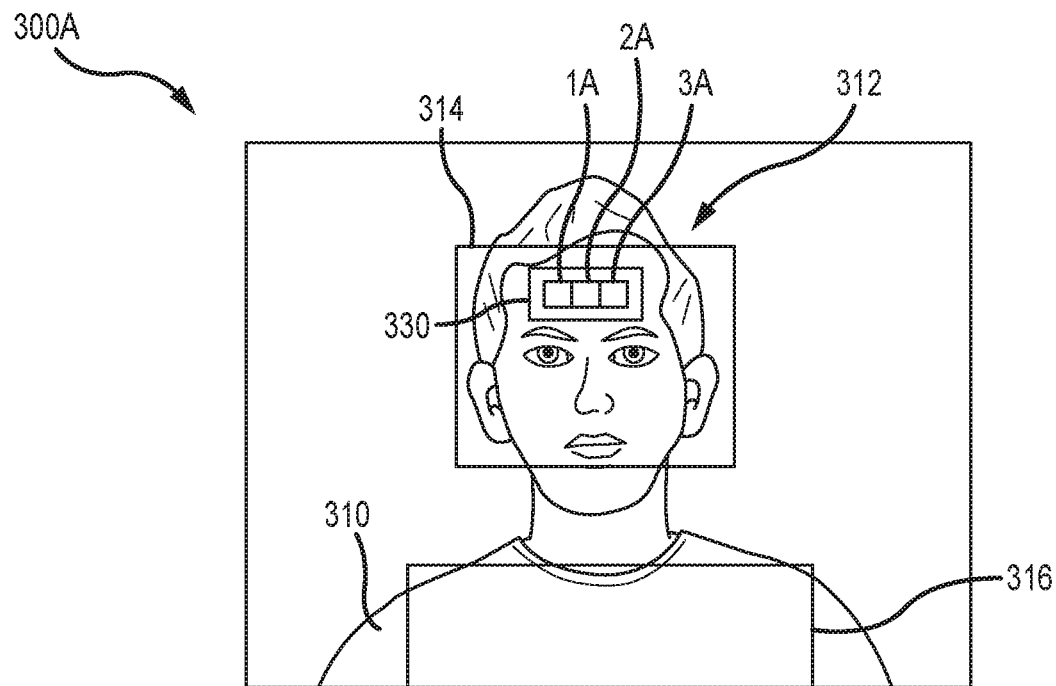
FIG. 3A depicts an image frame from a video signal according to an embodiment of the invention.
Figure 3B:
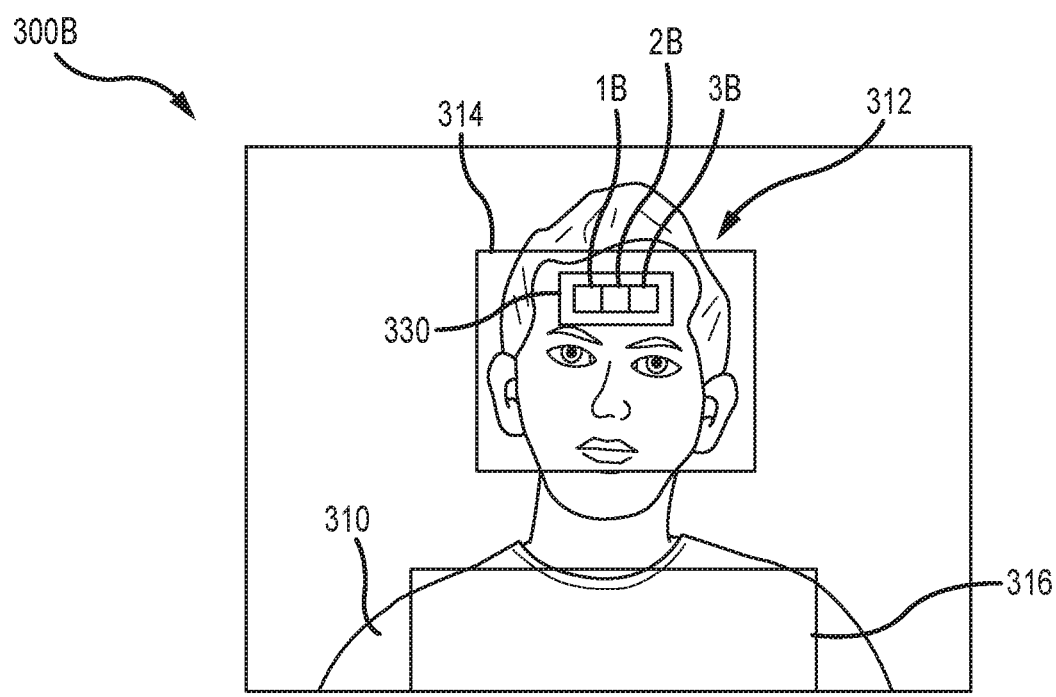
FIG. 3B depicts an image frame from a video signal according to an embodiment of the invention.

Two example image frames 300A and 300B are shown in FIGS. 3A and 3B, respectively. In an embodiment, these image frames are recorded by the system 200. Each image frame includes a patient's head 312 and upper torso 310 in the field of view. The processor has identified a head region 314 within each image frame 300A, 300B. The head region 314 includes at least a portion of the patient's head, such as the face. In some embodiments, the processor also infers a chest region 316, based on the size and location of the head region 314 and empirical ratios of head and chest sizes and shapes. For example, from a rectangular face region of width w and height h, a forehead region may be inferred of a size 0.7*w and 0.3*h, centered horizontally and positioned with its top edge moved down from the top of the face region by a distance 0.25*h. From the same rectangular face region, a chest region may also be inferred at a size of 2*w and 0.75*h, centered horizontally and positioned with its top edge below the bottom of the face region by a distance 0.25*h.

In an embodiment, the video camera records multiple sequential image frames (such as image frames 300A and 300B) that each include the head region 314 and chest region 316. The pixels or detected regions in these sequential images exhibit subtle modulations caused by the patient's physiology, such as heartbeats and breaths. In particular, the color components of the pixels vary between the frames based on the patient's physiology. In one embodiment, the camera employs the Red/Green/Blue color space and records three values for each pixel in the image frame, one value each for the Red component of the pixel, the Blue component, and the Green component. Each pixel is recorded in memory as these three values, which may be integer numbers (typically ranging from 0 to 255 for 8-bit color depth, or from 0 to 4095 for 12-bit color depth) or fractions (such as between 0 and 1). Thus, three one-dimensional vectors for each pixel in the field of view can be extracted from the video signal.

These Red, Green, and Blue values change over time due to the patient's physiology, though the changes may be too subtle to be noticed by the naked human eye viewing the video stream. For example, the patient's heartbeat causes blood to pulse through the tissue under the skin, which causes the color of the skin to change slightly—causing the value corresponding to the Red, Green, or Blue component of each pixel to go up and down. These changes in the pixel signals can be extracted by the processor. The regions within the field of view where these changes are largest can be identified and isolated to focus on the physiologic signal. For example, in many patients, the forehead is well-perfused with arterial blood, so pixels within the patient's forehead exhibit heartbeat-induced modulations that can be measured to determine the patient's heartrate.

To focus on this physiologic signal, the processor identifies a region of interest (ROI) within the image frame. In an embodiment, the region of interest includes exposed skin of the patient, such that the physiologic properties of the skin can be observed and measured. For example, in the embodiment of FIG. 3A, one region of interest includes a forehead region 330, which includes part of the patient's forehead. The processor determines the location of the patient's forehead within the head region 314, for example based on empirical ratios for a human face, and divides the forehead into distinct regions, for example, regions 1A, 2A, and 3A. In another embodiment, the region of interest does not include exposed skin. For example, in FIG. 3A, another region of interest includes the chest region 316 (which may be covered by clothing, bedding, or other materials on the patient). Pixels in this region may fluctuate with the patient's respiration rate, enabling that rate to be measured even without viewing exposed skin of the patient.

Within an individual region of interest, the Red components of the pixels in that region are combined together to produce one time-varying Red pixel signal from that region. The same is done for the Blue and Green pixels. The result is three time-varying pixel signals from each region, and these are plotted in FIG. 4A. The plots in FIG. 4A are derived from the regions 1A, 2A, 3A, and 316 of FIG. 3A. FIG. 4A also shows a plot labeled "Combined Forehead." The Combined Forehead plot shows the combined pixel signals from all three identified regions 1A, 2A, and 3A, meaning that the Red components from all three regions are combined together and plotted over time, as are the Green components and the Blue components. Different sub-sets of regions can be combined together to produce different combinations of pixel signals. Though three forehead regions 1A, 2A, and 3A are shown in FIG. 3A, the forehead, or any other area of interest, can be sub-divided into more or fewer regions, in various shapes or configurations. Pixel signals can be combined by summing or averaging or weighted averaging. In an embodiment, the combined pixel signals are obtained by averaging the Red (or Blue, or Green) color values of the pixels within the region, so that regions of different sizes can be compared against each other.

The pixels within a region may be combined together with a weighted average. For example, within a region, some pixels may exhibit stronger modulations than other pixels, and those stronger-modulating pixels can be weighted more heavily in the combined pixel signal. A weight can be applied to all of the pixels that are combined together, and the weight can be based on quality metrics applied to the modulating intensity signal of each pixel, such as the signal to noise ratio of the intensity signal, a skew metric, an amplitude of a desired modulation (such as modulations at the heart rate or respiration rate), or other measurements of the signal. Further, some pixels within the region may be chosen to be added to the combined pixel signal for that region, and other pixels may be discarded. The chosen pixels need not be adjacent or connected to each other; disparate pixels can be chosen and combined together to create the resulting signal.

The plots in FIG. 4A show a clear pattern of repeating modulations or pulses over time. The pulses in each region 1A, 2A, 3A and in the Combined Forehead plot are caused by the patient's heart beats, which move blood through those regions in the patient's forehead, causing the pixels to change color with each beat. The heart rate of the patient can be measured from these signals by measuring the frequency of the modulations. This measurement can be taken via a frequency transform of the signal (discussed below with reference to FIG. 4B) or via a pulse recognition algorithm that identifies each pulse in the signal (for example, by pulse size and shape, by zero crossings, maximums, or minimums in the derivative of the signal, and/or by checking the skew of the derivative of the signal to identify a pulse as a cardiac pulse, which has a characteristically negative skew). The modulations in the plot of the Chest region, in FIG. 4A, are caused by the patient's breaths, which cause the chest to move in correspondence with the breathing rate. The patient's breathing/respiration rate can be measured from this signal in the same way as just described for the heart rate (except for the skew approach). Respiration rate can be identified from a region of the patient that moves with each breath, such as the chest, but need not include exposed skin.

Figure 4B:
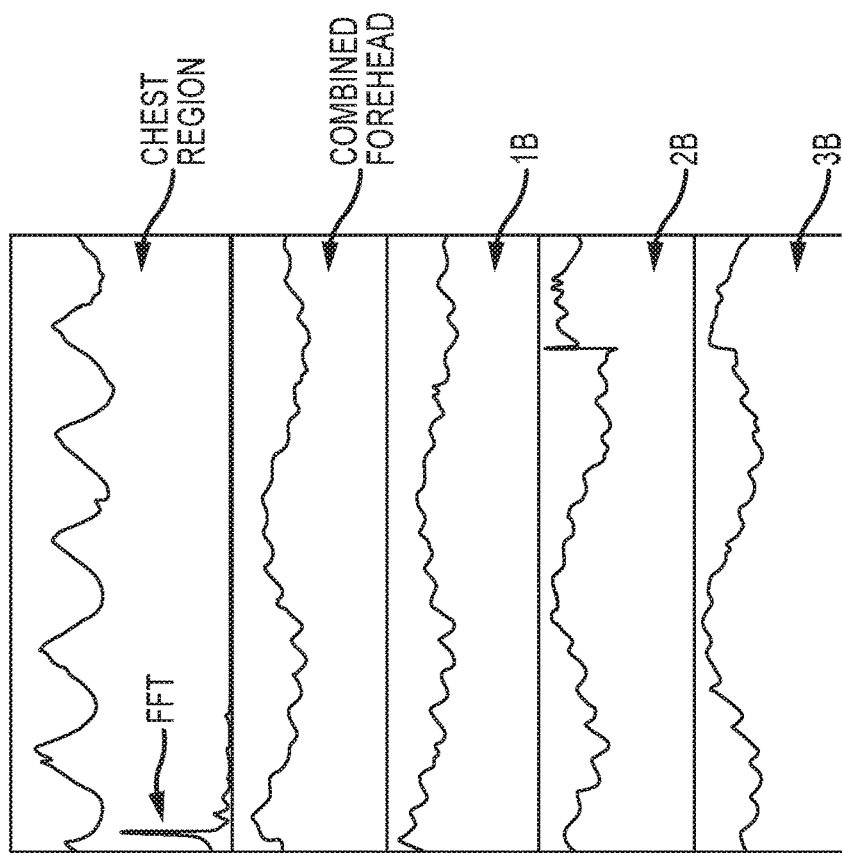
FIG. 4B depicts intensity signals from the video signal of FIG. 3B.
Figure 4A:
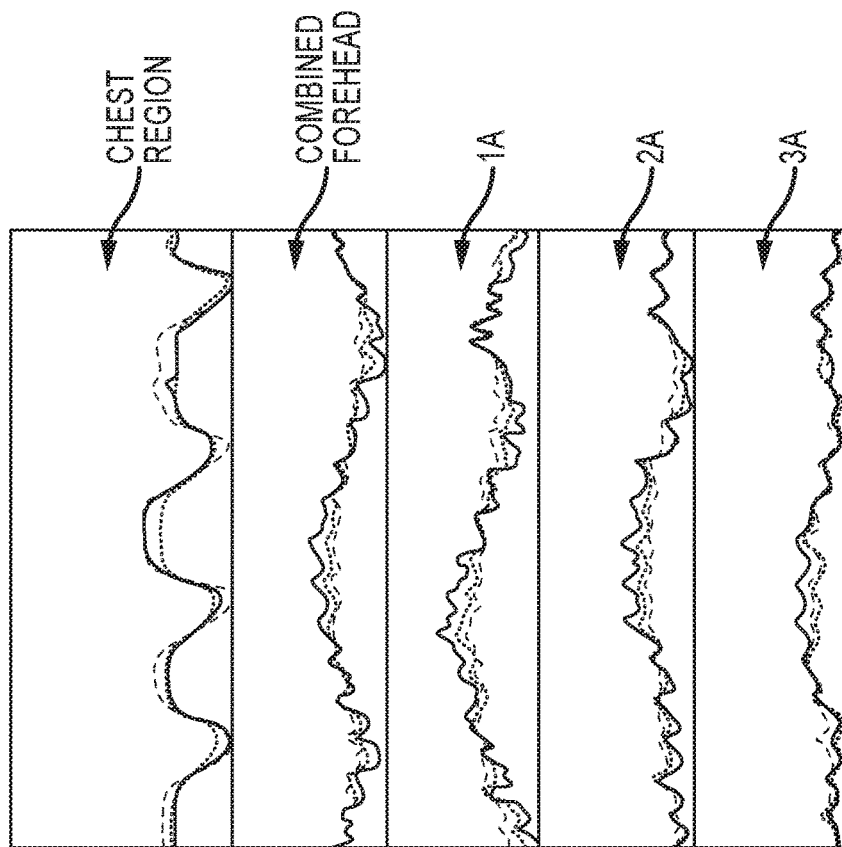
FIG. 4A depicts intensity signals from the video signal of FIG. 3A.
Figure 4C:
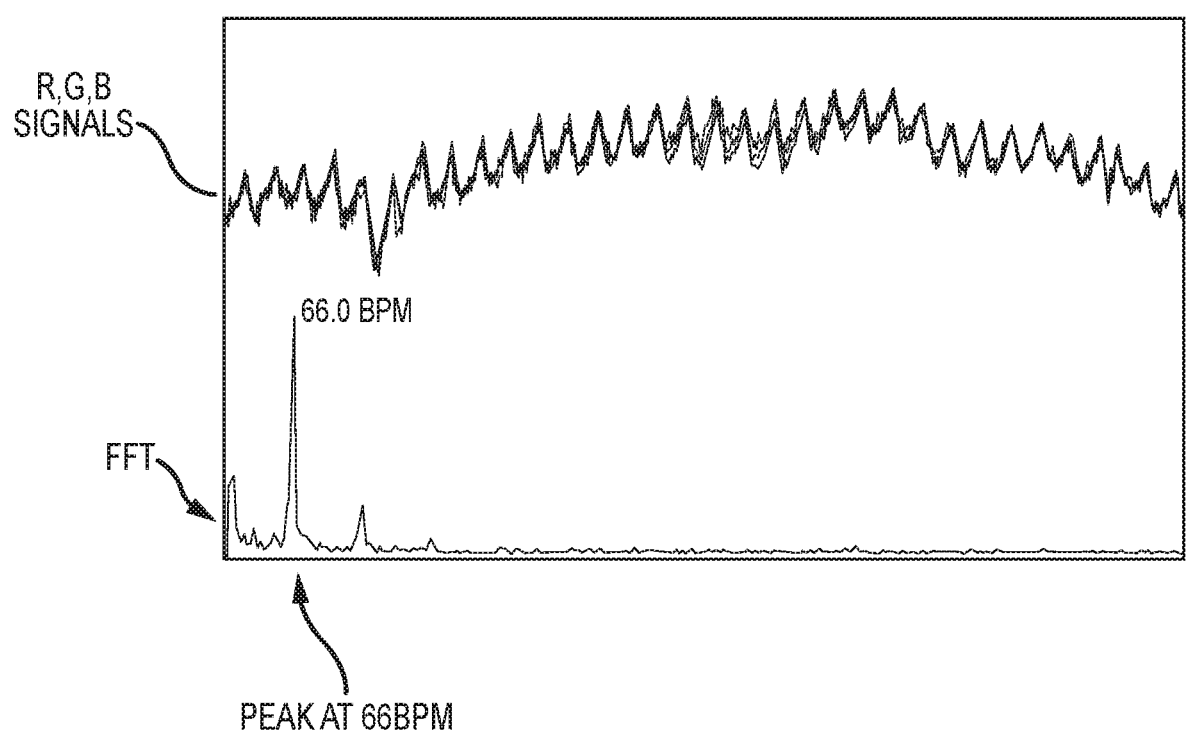
FIG. 4C depicts a chart of red, green, and blue intensity signals over time and a corresponding frequency transform according to an embodiment of the invention.

FIG. 4B shows plots of the pixel streams from the corresponding regions in FIG. 3B. However, in this case, the individual Red, Green, and Blue values within each region have been combined together, such as by summing or averaging, to produce one time-varying signal from each region instead of three separate Red, Green, and Blue signals. By viewing one combined signal from each region, the frequency of the heart rate or respiration rate may emerge more clearly. FIG. 4B also shows a Fast Fourier Transform (FFT) in the Chest Region plot. The FFT identifies the frequency content of the Chest signal, which reveals a primary frequency peak and harmonics. The primary frequency peak is the patient's respiration rate. Another example frequency transform of a pixel signal from a region of interest is shown in FIG. 4C. FIG. 4C shows three (Red, Green, and Blue) pixel signals over time and the FFT operation, which is applied to a 20-second window of the cross-correlated spectrum of all three signals. The FFT shows a strong peak at 66.0 beats per minute.

Though many embodiments herein are described with reference to pixels and pixel values, this is just one example of a detected light intensity signal. The light intensity signals that are detected, measured, or analyzed may be collected from larger regions or areas, without differentiating down to groups of pixels or individual pixels. Light signals may be collected from regions or areas within an image, whether or not such regions or areas are formed from pixels or mapped to a spatial grid. For example, time-varying light signals may be obtained from any detector, such as a camera or light meter, that detects a unit of light measurement over time. Such units of light measurement may come from individual pixels, from groups or clusters of pixels, regions, sub-regions, or other areas within a field of view. It should also be noted that the term "pixel" includes larger pixels that are themselves formed from aggregates, groups, or clusters of individual pixels.

In an embodiment, the Red, Green, and Blue values from the camera are converted into different color spaces, and the color space that provides the largest or most identifiable physiologic modulations is chosen. In an embodiment, color values are converted into a combination of a color value and a separate brightness value, so that changes in room brightness can be analyzed independently of color or hue. Alternative color spaces (such as YCrCb, CIE Lab, CIE Luv) can separate light intensity from chromatic changes better than the RGB color space. Processing the chromatic component in those spaces can reveal physiological modulation better than in RGB space, when overall scene light intensity is changing. Assessing signals based on chromatic channels in these spaces can increase the robustness of the algorithm and/or increase the range of conditions in which physiological signal extraction is possible. Though the Red/Green/Blue color scheme is often presented here in the examples, it should be understood that other color schemes or color spaces can be utilized by these systems and methods.

FIGS. 3A and 3B depict five regions of interest—three squares in the forehead, the combination of all three squares together, and one rectangular chest region. In other embodiments, regions of interest can have various shapes, configurations, or combinations. In another embodiment, the selected regions of interest may be non-adjacent to each other, or non-contiguous. Non-adjacent regions may include pixels that exhibit large modulations correlated with the patient's heartrate, as compared to the other regions. Regions located over large arteries may exhibit larger modulations with heartrate than other regions, for example. The intensity signals from non-adjacent regions are averaged together to create a combined signal, and the heartrate measured from that combined signal. Different non-adjacent regions may be chosen for other vital signs, such as respiration rate or oxygen saturation. In an embodiment, heart rate and oxygen saturation are calculated from a combined signal from a first group of non-adjacent pixels or regions, and respiration rate is calculated from a different combined signal from a second, different group of non-adjacent pixels or regions.

In an embodiment, regions of interest within the image frame are selected based on the modulations exhibited by the pixels in each region. Within an image frame, a sub-set of regions may be first identified as candidate regions for further processing. For example, within an image frame, an area of exposed skin of a patient is identified by facial recognition, deduction of a forehead region, user input, and/or skin tone detection. These areas are identified as the regions of interest for further processing. In an embodiment, facial recognition is based on Haar-like features (employing a technique that sums pixel intensities in various regions and differences between sums). A method includes identifying these regions of interest, extracting pixel signals from each region, quantifying the magnitude of physiological modulations exhibited by each pixel signal, selecting regions with strong modulations (such as modulations with an amplitude above a threshold), combining the selected pixel signals together (such as by averaging), and measuring a vital sign from the combined signal. In an embodiment, all sub-regions (such as grids) in the image (or a portion of the image, such as a patient region) are processed, and grid cells that exhibit coherent pulsatile components are combined to generate the pixel signals from which the physiologic measurements are taken.

Selecting non-adjacent regions enables the system to focus on the pixels or regions that carry the physiologic signal with the highest signal to noise ratio, ignoring other areas in the image frame that are contributing a relatively higher degree of noise, such as pixels that do not vary much with heart rate, but that might vary due to a passing shadow or patient movement. The system can focus on pixels that represent the desired vital sign, thereby increasing the signal-to-noise ratio (SNR) of the analyzed signal. With signals from several regions available, the signals with the strongest SNR can be chosen, and signals with weak SNR can be discarded. The chosen signals can be combined together to produce a signal with a strong physiologic component.

An example of a region of a good size for processing a physiologic signal is approximately one square centimeter (though more or less may also be useful—for example a whole forehead may be used, or an individual pixel). If far away from the subject, a camera may use less pixels. The selection of region size also depends on the resolution of the image, which may depend on the available hardware. Moreover, resolution and frame rate may be inter-related, in that increasing resolution may reduce frame rate. A compromise is necessary between high enough resolution to capture the modulating pixels, and a fast enough frame rate to track those modulations over time. Frame rates over 10 Hz are sufficient for cardiac pulses, and over 2-3 Hz for respiration modulations. Frame rates above about 50 or 60 frames per second are generally less subject to aliasing frequencies introduced by artificial lighting. Sampling from a few hundred pixels (such as over 200 or over 300 pixels) has been sufficient to isolate a physiologic modulation above ambient noise.

The selected regions of interest can change over time due to changing physiology, changing noise conditions, or patient movement. In each of these situations, criteria can be applied for selecting a pixel, group of pixels, or region into the combined signal. Criteria are applied to enhance the physiologic signals by reducing or rejecting contributions from stationary or non-stationary non-physiologic signals. Criteria can include a minimum SNR, a minimum amplitude of physiologic modulations, a minimum variability of the frequency of modulations (to reject non-physiologic, static frequencies), a skew metric (such as modulations that exhibit a negative skew), pixels with values above a threshold (in the applicable Red, Green, or Blue channel), pixels that are not saturated, or combinations of these criteria. These criteria can be continually applied to the visible pixels and regions to select the pixels that meet the criteria. Some hysteresis may be applied so that regions or pixels are not added and removed with too much chatter. For example, pixels or regions must meet the criteria for a minimum amount of time before being added to the combined signal, and must fail the criteria for a minimum amount of time before being dropped. In another example, the criteria for adding a pixel or region to the combined signal may be stricter than the criteria for removing the pixel or region from the combined signal.

For example, in an example involving motion, when the patient turns his or her head, the regions of interest that previously demonstrated heart rate with the best amplitude are no longer visible to the camera, or may be covered in shadow or over-exposed in light. New regions of interest become visible within the field of view of the camera, and these regions are evaluated with the criteria to identify the best candidates for the desired vital sign. For example, referring to FIG. 3A, cells or groups of pixels at the edges of the forehead region 330 can be added or removed from the combined signal during motion as they enter and exit the forehead region. This method enables the monitoring system to continue to track the vital sign through movement of the patient, even as the patient moves or rotates with respect to the camera.

Selected regions may also change over time due to changing physiology. For example, these regions can be updated continually or periodically to remove pixels that do not satisfy the criteria for vital sign measurement, and add new pixels that do satisfy the criteria. For example, as the patient's physiology changes over time, one region of the forehead may become better perfused, and the pixels in that region may exhibit a stronger cardiac modulation. Those pixels can be added to the combined light signal to calculate the heart rate. Another region may become less perfused, or changing light conditions may favor some regions over others. These changes can be taken into account by adding and removing pixels to the combined signal, to continue tracking the vital sign.

Selected regions may also change over time due to changing noise conditions. By applying the criteria over time, pixels or regions that become noisy are removed from the combined light intensity signal, so that the physiologic signal can continue to be monitored via pixels or groups that are less noisy. These updates can be made continually.

The combined light signal can be used to calculate statistics, such as an amplitude of the physiologic frequency (in the time or frequency domain), a variability of the frequency over time, a variability of the intensity or color of the selected pixels over time, a skew of the modulations, or a signal to noise ratio. Skew is a useful metric because cardiac pulses tend to have a negative skew. Thus, modulations of pixels that exhibit a negative skew may be more likely to be physiologic. In an embodiment, one or more statistics are calculated, and then used to apply a weight to each color signal (from an individual pixel or from a region) that is being combined. This method results in a weighted average that applies more weight to the pixels that exhibit modulations that are stronger or more likely to be physiologic. For example, pixels that modulate with a strongly negative skew, or a high signal to noise ratio, can be weighted more heavily. The criteria used to select regions can also be used to assign weights; for example, regions or pixels that meet a first, stricter set of criteria may be combined with a first, higher weight, and regions or pixels that meet a second, looser set of criteria may be combined with a second, lower weight.

In an embodiment, a weight can also be applied to the vital sign that is calculated from the combined light signal. Each time the vital sign is calculated, a weight can be determined based on current quality measures or statistics from the combined light signal. The newly calculated vital sign is then added to a longer-term running average, based on the weight. For example, the patient's heart rate can be calculated from the combined light signal once per second. An associated weight can be calculated based on the criteria applied to the combined light signal. The weight is reduced when statistics indicate that the light signal may be unreliable (for example, the amplitude of the modulations drops, or the frequency becomes unstable, or the intensity changes suddenly) and increased when statistics indicate that the light signal is reliable.

Figure 5A:
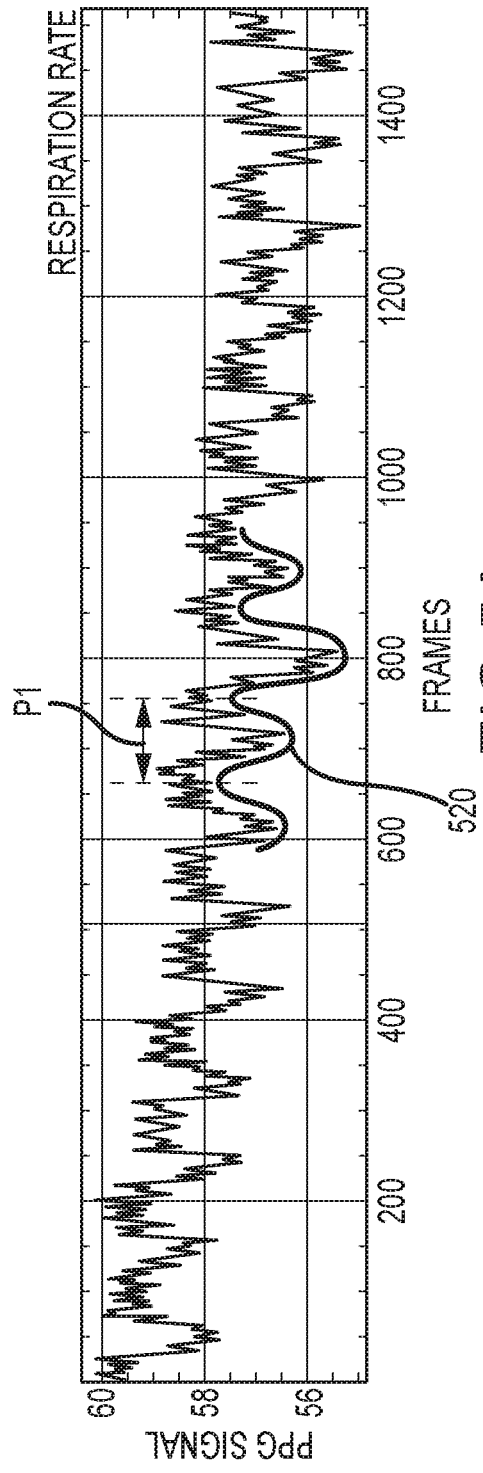
FIG. 5A is a chart of an intensity signal from a first region of interest according to an embodiment of the invention.
Figure 5B:
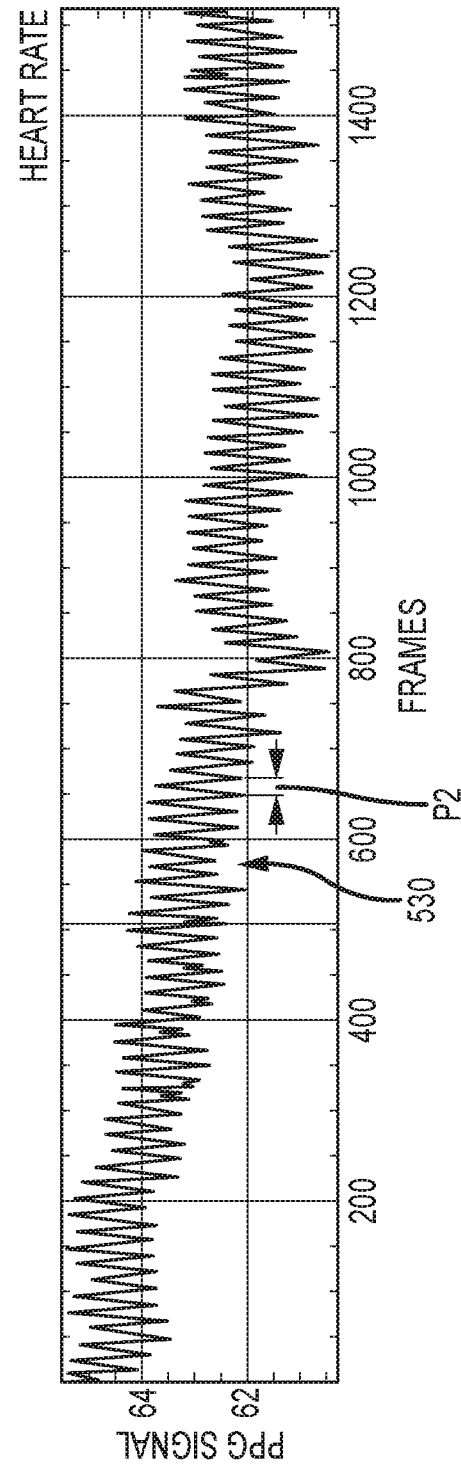
FIG. 5B is a chart of an intensity signal from a second region of interest according to an embodiment of the invention.

Furthermore, different combinations of pixels (and/or regions) may be selected for different vital signs of the patient. For example, a first group of pixels and/or regions is summed together to produce a signal that modulates with heart rate, and a second group of pixels and/or regions is summed together to produce a signal that modulates with respiration rate. This approach is demonstrated in FIGS. 5A and 5B, which each show a light intensity signal over the same span of time from the same video signal for the same patient, from different regions, such as groups of pixels. The pixels chosen for the plot in FIG. 5A exhibit relatively large fluctuations correlated with the patient's respiration. This is shown by the large baseline modulations 520, with period P1, in the plotted pixel signal. The frequency of the modulations 520 is the patient's respiration rate, such as 5-20 breaths per minute. By contrast, the pixels chosen for the plot in FIG. 5B do not fluctuate as dramatically with the patient's respiration, but they do fluctuate with the patient's heart rate, as shown by the modulations 530 with shorter period P2. The frequency of these modulations is the patient's heart rate, such as 40-200 beats per minute. These two different plots shown in FIGS. 5A and 5B reflect different vital signs of the patient, based on the same video stream from the same camera taken over a single period of time. By creating combined pixel signals from appropriately selected pixels or regions, various physiologic signals emerge from the video images.

In an embodiment, a user can view a video image, specify a region of interest, and drag and drop the region across the video image to view changes in modulations in real-time. For example, referring to FIG. 15A, a monitor 1508 displays a video image on a display screen 1562 that accepts inputs from a user. A user can use mouse pointer 1509 (or other input) to highlight a first area 1507A, and view the resulting pixel signals such as the signal shown in FIG. 5A and vital signs measured from that signal. The user can then drag and drop the area of interest to a second area 1507B and view the resulting signal and vital signs, such as the signal shown in FIG. 5B. In this way, the user can view in real time how the modulations of the signal change based on the selected area of interest. In area 1507A, the video signal shows strong respiration modulations (see FIG. 5A), while in area 1507B, the video signal shows strong cardiac modulations (see FIG. 5B). The user can view the video signal in real-time as it moves along the path from 1507A to 1507B, to see how the modulations change as the region of interest moves. The user can also view the pixel signals shown in FIGS. 5A and 5B at the same time, to evaluate different vital signs from different regions of interest, at the same time.

Accordingly, in an embodiment, a method is provided for measuring different vital signs from different regions. These groups can include individual pixels, disparate pixels, contiguous regions, non-contiguous regions, and combinations of these. Pixels combined into one group exhibit a common modulation, such as a frequency of modulation of color or intensity. For example, heart rate can be measured from the frequency of modulation of a first group of pixels, and respiration rate can be measured from the frequency of modulation of a second group of pixels. Oxygen saturation can be measured from either group; in one embodiment, oxygen saturation is measured from the pixels that show strong modulation with heart rate.

In an embodiment, a method for monitoring a patient's heart rate includes generating a video signal from a video camera having a field of view encompassing exposed skin of a patient. The video signal includes a time-varying intensity signal for each of a plurality of pixels or regions in the field of view. The method includes extracting the intensity signals within a region of the field of view, and transforming the intensity signal into the frequency domain to produce a frequency signal. The region may be selected based on a strength of modulations of intensity signals in the region. The region may include non-adjacent areas or pixels. Over a sliding time window, peaks in the frequency signal are identified, and then over a period of time (such as one second), the identified peaks are accumulated. The method includes selecting a median frequency from the identified peaks, and updating a running average heart rate of a patient, which includes converting the median frequency into a measured heart rate and adding the measured heart rate to the running average. The updated average heart rate is output for display. The method may also include removing identified peaks from the accumulated peaks when they reach an age limit. The method may also include discarding frequency peaks outside of a physiologic limit, or discarding the measured heart rate when it differs from the average heart rate by more than a defined amount. The method may also include discarding frequency peaks if they are subharmonics of already identified peaks.

According to an embodiment of the invention, the Red/Green/Blue pixel streams from identified areas of the patient's exposed skin can be used to determine arterial oxygen saturation (SpO2). Traditional pulse oximeters employ contact-based sensors, which include two emitters (typically light emitting diodes, LED's) and a photodetector. The emitters are positioned on the sensor to emit light directly into the patient's skin. The emitters are driven sequentially, so that light of each wavelength can be separately detected at the photodetector, resulting in two time-varying light intensity signals. The wavelengths are chosen based on their relative absorption by oxygenated hemoglobin in the blood. Typically one wavelength falls in the red spectrum and the other in infrared. The patient's arterial oxygen saturation can be measured by taking a ratio of ratios (ROR) of the two signals—that is, by taking a ratio of the alternating component (AC) of each signal to its direct, non-alternating component (DC) and dividing the red ratio by the infrared ratio.

In a video-based system, the Red/Green/Blue pixels or regions detected by the camera provide three light intensity signals that potentially can be used in a similar ratio of ratios calculation, such as by dividing the ratios of any two of the three signals. However, many standard video cameras do not detect light in the infrared wavelengths. Moreover, for many video cameras, the wavelengths of light detected in each of the Red, Green, and Blue components overlap. For example, the video camera 214 (see FIG. 2A) may include an image sensor with broad spectrum red, green, and blue detectors. The wavelengths detected by these detectors overlap, and are not chosen specifically for their relative absorption by oxygenated hemoglobin. As a result, measuring a ratio of ratios from two of the three signals does not provide an absolute, calibrated SpO2 value. However, such a ratio of ratios can be used to track the trend of the patient's actual SpO2 value.

In an embodiment, the video-based non-contact monitoring system identifies acute hypoxia in monitored patients, by identifying episodes of decreased oxygen saturation. The system provides continuous monitoring of vital signs such as video-based SpO2, rather than discrete, periodic spot-check readings. This continuous monitoring, via either trending or calibrated video SpO2, enables the system to identify clinical conditions such as acute hypoxia, and repeated interruptions in airflow.

Figure 5C:
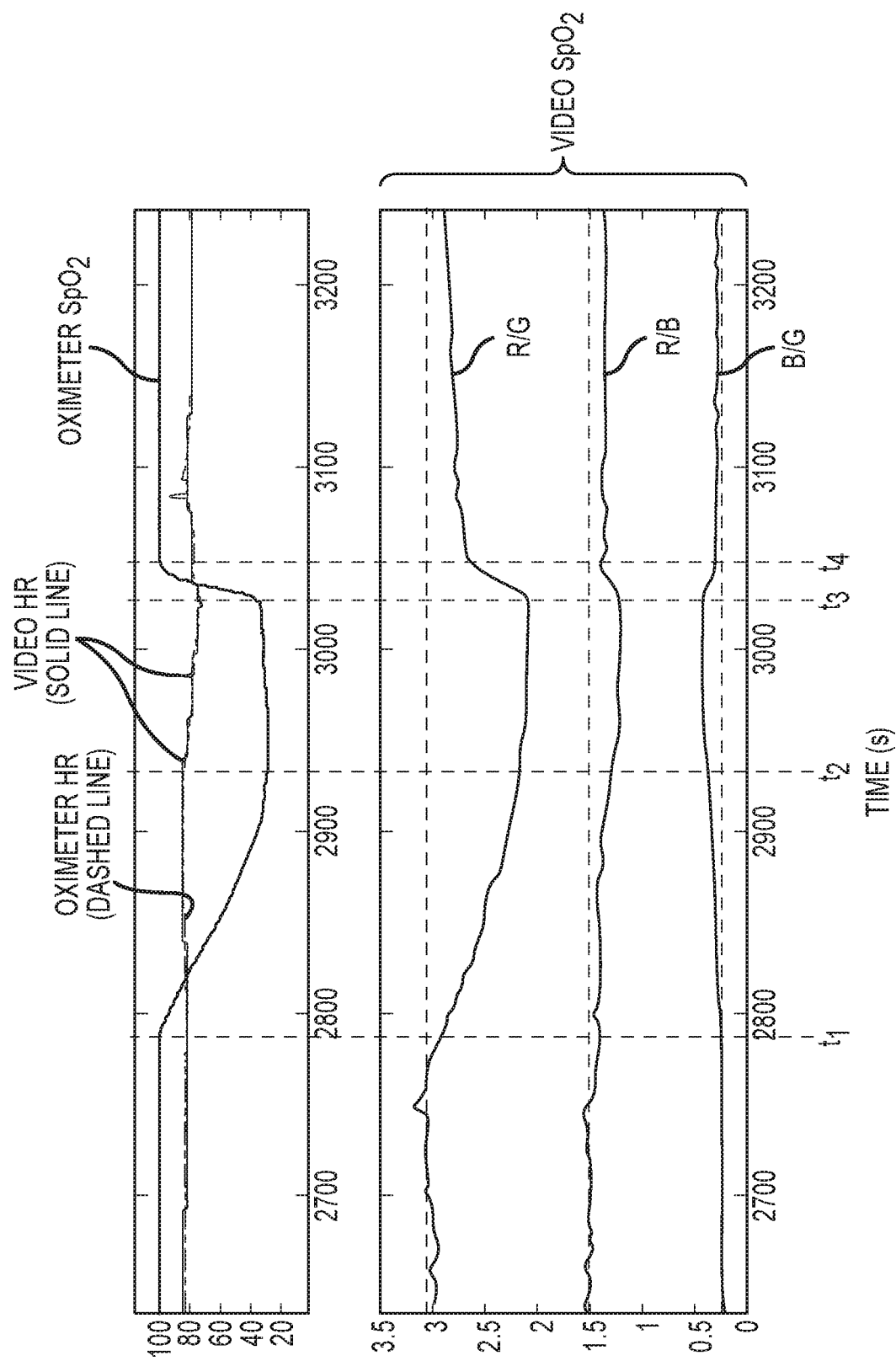
FIG. 5C is a chart of contact-oximeter-based and video-based vital signs (heart rate and SpO2) over time according to an embodiment of the invention.

Such a trend is shown in FIG. 5C. The top plot in FIG. 5C shows an SpO2 value from a calibrated, contact-based pulse oximeter. It also shows two heart rate signals, one taken from the same pulse oximeter and the other from a video signal. It is readily apparent that the video-based heart rate signal tracks the oximeter-based heart rate signal very closely, providing good absolute correlation.

The bottom plot in FIG. 5C shows three different SpO2 values from a video signal, one for each pair of signals. The top trace is from a ratio of ratios calculation of the Red and Green signals, the middle is the Red and Blue signals, and the bottom is the Green and Blue signals. These three traces can be compared with the calibrated SpO2 value plotted above, from the conventional contact pulse oximeter. It is clear from FIG. 5C that all three traces correlate with the calibrated SpO2 plot, in that they trend up or down in proportion to the calibrated SpO2 plot. However the absolute values (shown in the y-axes in FIG. 5C) of the video-based SpO2 traces do not match the calibrated SpO2 value itself. The calibration of the SvidO2 against SpO2 may be performed by linear regression, whereby the coefficients of the regression model are applied to the SvidO2 to estimate the absolute SpO2 values.

In an embodiment, the video-based SpO2 measurement is used as a trend indicator, rather than as a measurement of an accurate SpO2 numerical value. For example, it is apparent from the Blue-Red trace that the SpO2 value remains stable until time t1, begins to change at time t1, decreases until time t2, remains stable at low oxygenation until time t3, increases again until time t4, and thereafter remains stable again. The Blue-Red trace can thus be used as a trend indicator, to provide an alert that the patient's SpO2 value is changing, and can even indicate whether the SpO2 value is increasing or decreasing, and an indication of the rate of increase or decrease. This information can be used to provide an early warning to a caregiver that the patient needs attention, such as by attaching a traditional contact-based pulse oximeter to obtain a numerically accurate reading of the patient's SpO2 value which can be used to determine a diagnosis or treatment.

In another embodiment, the SpO2 value measured from a pair of the Red/Green/Blue pixel streams is calibrated to an accurate numerical value. Calibration can be done by comparing the video-based SpO2 value to the value from a reference contact-based oximeter, to identify an offset between them. This offset is used to determine a scaling factor that is applied to the ROR calculation from the video signal. For example, the scaling factor can be a coefficient multiplied to the video ROR, or an offset added or subtracted from the video SpO2, or both. This offset and/or coefficient can be used until the next recalibration. Recalibration can be done when a set time has expired, or when the video SpO2 trend shows a marked change in SpO2.

Figure 5D:
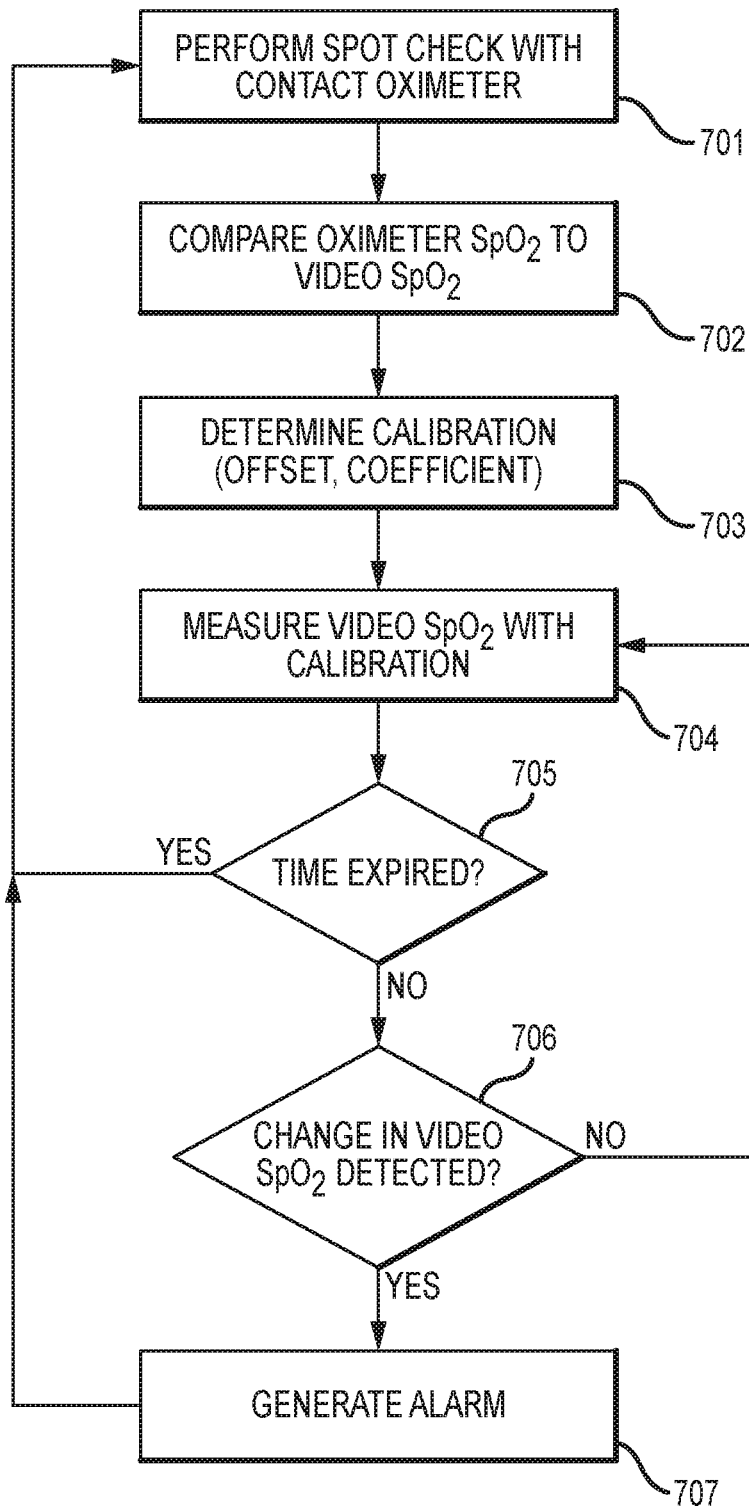
FIG. 5D is a flowchart of a method of calibrating video-based pulse oximetry according to an embodiment of the invention.

FIG. 5D shows a method of calibrating a video-based SpO2 measurement, according to an embodiment of the invention. The method includes performing a spot check with a contact oximeter at 701, comparing the oximeter SpO2 to the video SpO2 (also called $S_{vid}O2$) at 702, and determining the calibration between the two values (such as an offset, scaling factor, and/or coefficient) at 703. The method then includes measuring SpO2 from the video signal with the calibration at 704. At 705, a timer is used to prompt re-calibration. For example, the timer may be set to expire in 15 minutes, or one hour, or two hours, or other time durations desired by the caregiver. If the time has expired, the method returns to 701; if not, the method continues to 706, where the video SpO2 value is compared to a threshold to identify changes. If the video SpO2 value crosses the threshold, the method includes sounding an alarm (such as an audible sound and/or a visible alert) at 707, and prompting re-calibration at 701. If not, the method returns to continue measuring at 704. The threshold used to detect a change at 706 can be set by the caregiver to identify changes in video SpO2 that may indicate a clinically significant change in the patient's physiology, for further diagnosis or treatment.

When calibration or re-calibration is not available, the monitor may continue to calculate video SpO2 to identify trends. The trend from the video SpO2 may be used to trigger an alarm when the trend shows that SpO2 is rapidly changing or has crossed an alarm threshold. Clinically relevant patterns (such as repeated desaturations) may also be detected from the video SpO2 signal, between or in the absence of re-calibrations.

Figure 5E:
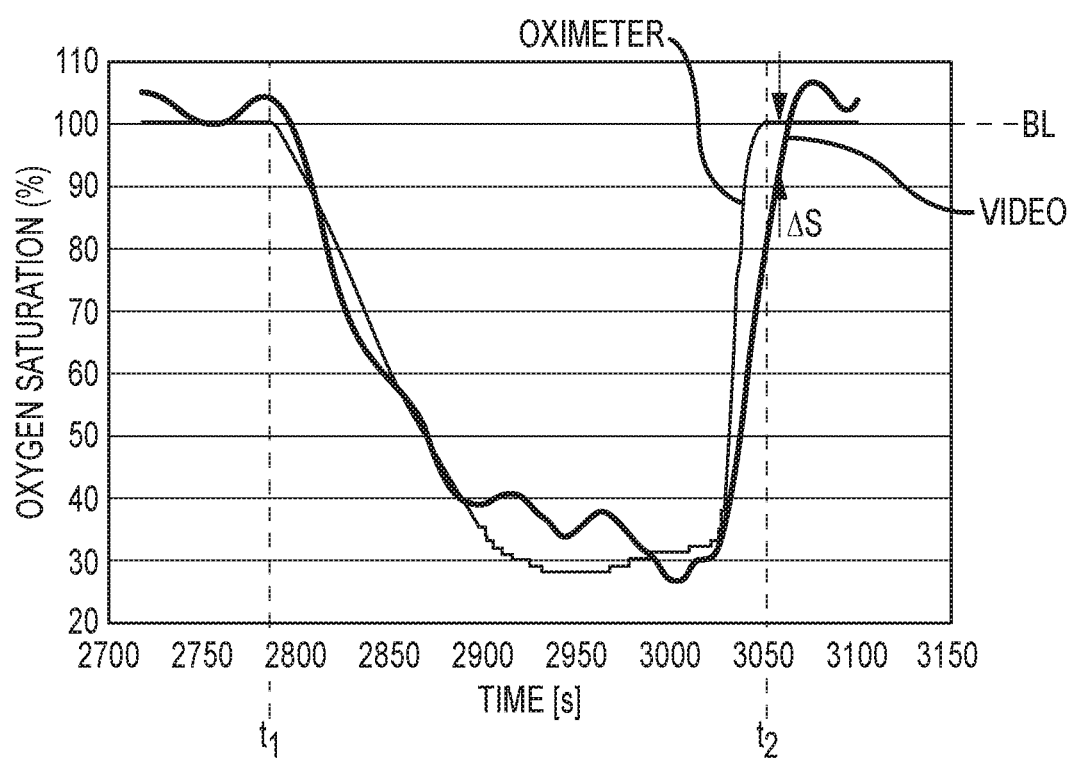
FIG. 5E is a chart of video-based and contact-based measurements of arterial oxygen saturation over time, including a desaturation event, according to an embodiment of the invention.

When the video-based SpO2 value is calibrated to an accurate measure of oxygen saturation, it can be tracked from there to measure the patient's actual SpO2 value. An example of this is shown in FIG. 5E, which plots two SpO2 values, one from a traditional contact-based pulse oximeter, and the other from a calibrated video-based pulse oximeter. The video-based SpO2 value in this example is taken from the Red and Green signals, and then calibrated with an absolute SpO2 value as described above. Once calibrated, it is clear from FIG. 5E that the video-based SpO2 value tracks the patient's absolute SpO2 value closely. The data presented in FIG. 5E was collected during a clinically-relevant desaturation event in which the subject's oxygen saturation dipped and then recovered.

Though the video-based SpO2 measurement can be calibrated from a contact-based pulse oximeter, the video-based SpO2 measurement may exhibit different behavior over time, as compared to a traditional contact-based oximeter. These differences may arise due to the differences in filtering characteristics between the contact-based oximeter and video camera, and/or differences in the light waveforms detected by a remote video as compared to a contact-based sensor, and/or other factors. As an example, the light detected by a remote video camera may be reflected from a shallower depth within the patient's tissue, as compared to contact-based oximetry, which utilizes a contact sensor to emit light directly into the patient's tissue. This difference in the light signal can cause the morphology of the video-detected waveform to differ from a contact-based waveform. As another example, the light detected by a remote video camera is more susceptible to ambient light noise incident on the surface of the region being monitored.

As a result, the SpO2 measurement from the video-detected waveform exhibits some differences from the contact-based SpO2 measurement, even when the two are first calibrated together. An example of this behavior is evident in FIG. 5E. Between times t1 and t2, the subject's oxygen saturation drops and then recovers to a baseline level BL. Both waveforms track this trend, but the video-based measurement is slower than the contact-based measurement to return to baseline. The result is a difference, labeled ΔS (delta saturation) between the two measurements. Because this behavior of the video-based measurement is known, it can be corrected for, by adjusting the value upward during an increasing trend. This adjustment can be tailored based on empirical data. An adjustment may be made by finding the relationship (mapping) between the video-based SpO2 and the contact-based (oximeter) SpO2. This relationship may then be coded within the video system to mimic the oximeter-based SpO2.

In an embodiment, the video-based non-contact monitoring system identifies acute hypoxia in monitored patients, by identifying episodes of decreased oxygen saturation. The system provides continuous monitoring of vital signs such as video-based SpO2, rather than discrete, periodic spot-check readings. This continuous monitoring, via either trending or calibrated video SpO2, enables the system to identify clinical conditions such as acute hypoxia, and repeated interruptions in airflow.

In an embodiment, the video-based non-contact monitoring system utilizes a camera that detects light across the visible spectrum. In an embodiment, the camera detects light in only a portion of the visible spectrum, and/or in the infrared spectrum as well.

Figure 6A:
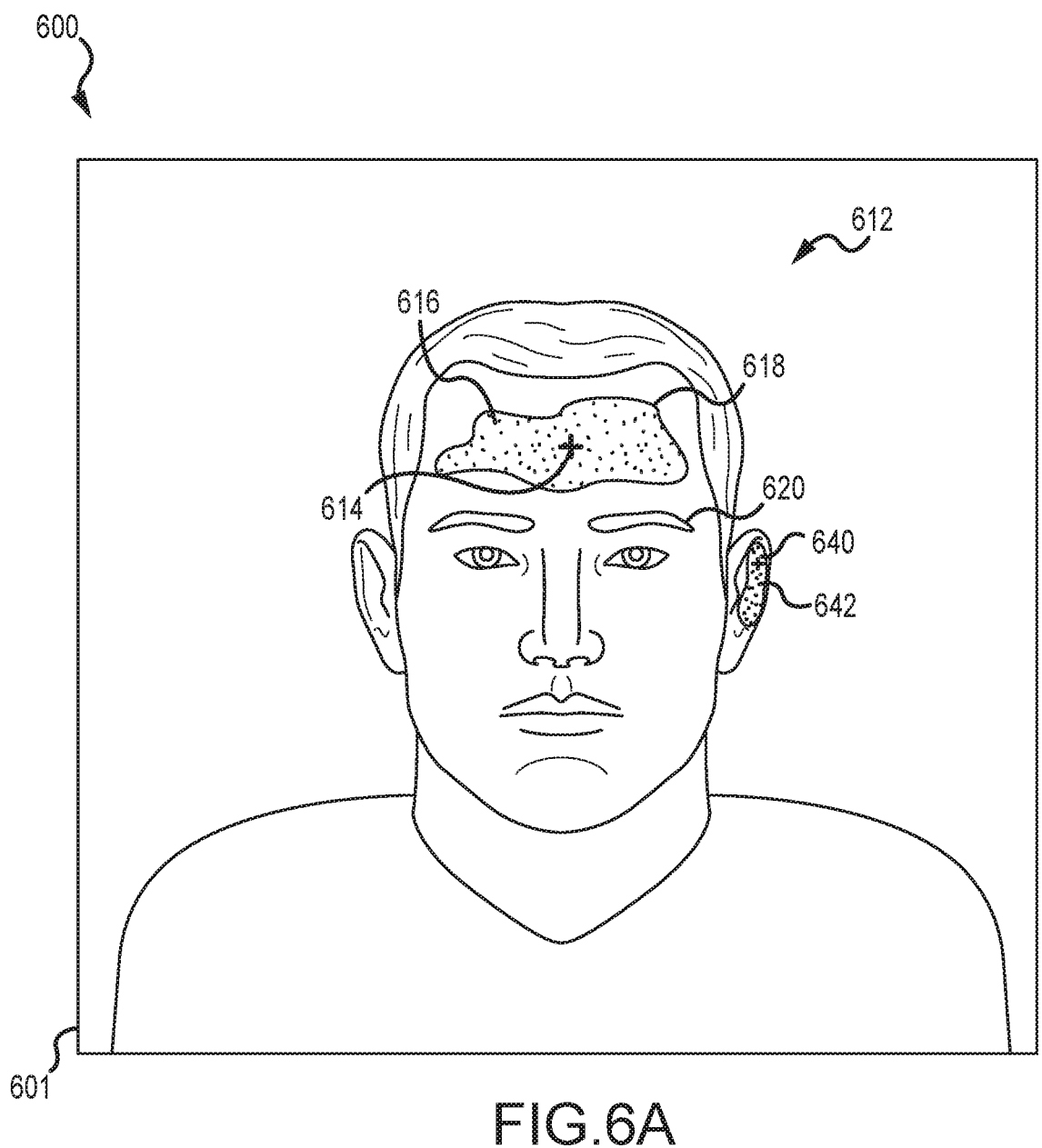
FIG. 6A depicts an image frame from a video signal, with a seed point for a flood fill region, according to an embodiment of the invention.

An image frame 600 representing a video signal is shown in FIG. 6A, according to an embodiment. A video signal exposed to a patient is acquired by a video camera, as described above, and passed to a monitor for analysis. The monitor receives the video signal and analyzes incoming images, such as the image frame 600, to recognize areas that are physiologically relevant, extract a light intensity signal from such an area, and measure a vital sign from the extracted intensity signal. Though only one image frame 600 is shown in FIG. 6A, it should be understood that the methods apply to moving image frames from a time-varying video signal. The image frame 600 views a field of view 601, which is exposed to a patient 612. The patient may have exposed skin within the field of view, in order to measure certain vital signs such as SpO2, but this is not required, as some vital signs can be measured from clothed areas (such as respiration rate from a clothed chest region).

In an embodiment, a flood fill method is employed in order to recognize a physiologically relevant portion of the image frame. Referring to FIG. 6A, the image frame is analyzed to identify a seed point 614, which identifies an initial point for the flood fill region. This seed point 614 can be identified in different ways, depending on the situation and the type of monitoring being done. In an embodiment, a clinician, such as a doctor or nurse, taps on the image to identify the seed point, such as by tapping on the patient's forehead. The location of the clinicians' touch input on the image is saved as the seed point. In another embodiment, the monitor employs a facial recognition process to determine whether a face is present in the image, and then to infer the likely location of a forehead (as discussed further below with respect to FIG. 6B). A point within the inferred forehead region, such as at or near the center of the inferred forehead region, is chosen as the seed point.

The flood fill method fills a contiguous region 616 from the seed point 614. The contiguous region 616 may also be referred to as the flood filled region or the flood field. This region is identified through a process that evaluates pixels adjacent the seed point 614, selects those pixels that share one or more common characteristics with the seed point, and then repeats the process for the selected pixels. This process repeats until a boundary 618 is reached, where the pixels lack the common characteristic(s). The contiguous region 616 ends at this boundary 618. In an embodiment, the characteristic that defines the contiguous region and excludes the boundary is the color values of one or more pixels at the seed point 614. For example, the values of one or more of the Red, Green, or Blue pixels at the seed point 614 are stored, and then the flood fill operation adds neighboring pixels whose color values are within a tolerance of the seed point 614. The area around the seed point may be blurred or smoothed slightly to avoid the instance where the seed point is an outlier with color values too far removed from its neighbors. The smoothed color values at or around the seed point are used to set the range for the flood fill method, which can then be applied to the original, full resolution video image.

The purpose of the flood fill method is to identify a contiguous region that spans a portion of the patient's exposed skin, where a physiologic signal can be extracted, and that stops at a boundary 618 such as hair, bandages, eyes, or other features where the physiologic signal is missing or attenuated. The flood fill method automatically stops at those boundaries if the color values differ from the seed point 614 by more than the allowed tolerances. The result is a contiguous region with pixels that share similar color characteristics, and therefore are more likely to provide a physiologic signal with a high signal to noise ratio. An example tolerance can range from 0.5% to 4%. Tolerances are affected by the subject's skin tone, the ambient lighting, and the color depth of the camera, and can be adjusted to each situation.

Other characteristics can also be used to add or exclude neighboring pixels from the contiguous region. For example, the frequency content of the pixels at each point can be evaluated, and those that exhibit an intensity modulation at the same frequency as the seed point, or within a certain tolerance, are added to the contiguous region, and otherwise rejected as a boundary. This approach looks for pixels that modulate with the patient's pulse rate, or respiration rate, and adds those modulating pixels to the contiguous region, to produce a region that shows a strong physiological signal. These modulations can also be subject to an amplitude threshold, such that pixels that exhibit the modulation are added to the contiguous region only if the modulation exceeds the threshold, in order to exclude pixels that are modulating at the same frequency but only at a low amplitude. Those pixels might be adding more noise than signal, or may be near enough to a boundary (such as an eyebrow) that the physiologic signal is beginning to fade.

Another example is light intensity. Pixels whose intensity exceeds a threshold can be added to the contiguous area, and dimmer pixels are excluded as forming the boundary. This characteristic might be used where the pixels are greyscale, or where a filter is employed in front of the camera, passing pixels within a narrow color or wavelength range. Another example characteristic is signal to noise ratio (SNR). Where a physiologic signal is present, such as pixel intensity modulating with pulse rate or respiration rate, those modulations (the signal) can be compared to the baseline intensity level (the noise) to determine SNR, and only those pixels whose SNR exceeds a threshold are added to the contiguous region.

In another embodiment, a combination of characteristics is utilized to include or exclude pixels with the flood fill method. For example, two or more characteristics can be evaluated, and all must pass their respective thresholds or checks in order for the new pixel to be added. Alternatively, a subset, such as two out of three, or three of four, or one required characteristic as well as two of three others, or other subsets and combinations, can be used as the evaluation. Alternatively, an index or combined score can be created based on various characteristics, such as by averaging or weighted averaging, to create a threshold.

Referring again to FIG. 6A, an example of a boundary is an eyebrow region 620. As the flood fill region 616 expands out from the seed point 614, pixels across the patient's forehead that meet the applied characteristic(s) are added to the region 616, and then neighboring pixels of those added pixels are evaluated, until reaching the eyebrow region 620. At this region, the pixels lack the common characteristic, such as by changing color or intensity or failing to modulate with the patient's pulse rate. These pixels are not added to the region, and the region ends at that boundary. The process is an additive process that is complete when no neighboring pixels fit the set tolerances. Once the contiguous region 616 is identified, the intensity signal from this region can be extracted, and a vital sign (such as pulse rate, respiration rate, and/or SpO2) can be measured from the time-varying intensity signal, as discussed elsewhere herein.

Figure 6B:
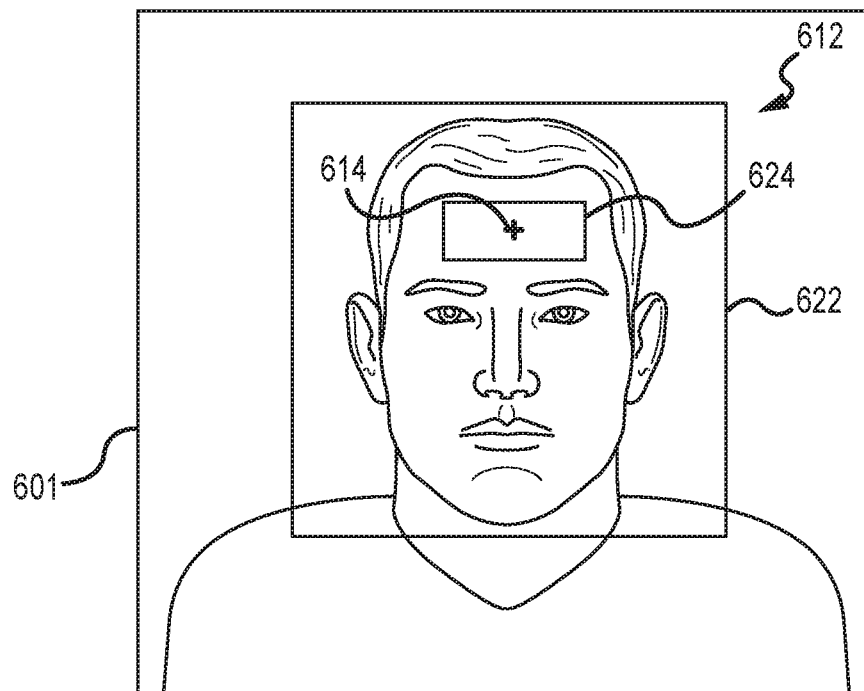
FIG. 6B depicts an image frame from a video signal, with facial recognition, according to an embodiment of the invention.

In FIG. 6B, a facial recognition process is employed to identify the seed point 614. A facial feature such as a nose bridge, eye region, or other feature is recognized, and then the first seed point is located relative to the recognized facial feature. For example, the field of view 601 is exposed to at least a portion of the patient 312, and a commercially available facial recognition tool is utilized to identify a face box 622. The face box can be identified based on a recognized pattern of facial features and inferred head size and ratios. Facial recognition software that can accomplish these steps is commercially available, such as the Viola-Jones algorithm, with feature trackers such as Kanade-Lucas-Tomasi (KLT). A forehead location 624 can then be inferred from the face box 622, based on empirical ratios. Then, the seed point 614 can be assigned at or near a center, or within any part of, the forehead location 624. After the seed point is assigned, the flood fill method is used to produce the contiguous region 616 of FIG. 6A. In an embodiment, the facial recognition process can include a user input that specifies a location of a facial feature (as described below in more detail with reference to FIGS. 15A-D).

Figure 6C:
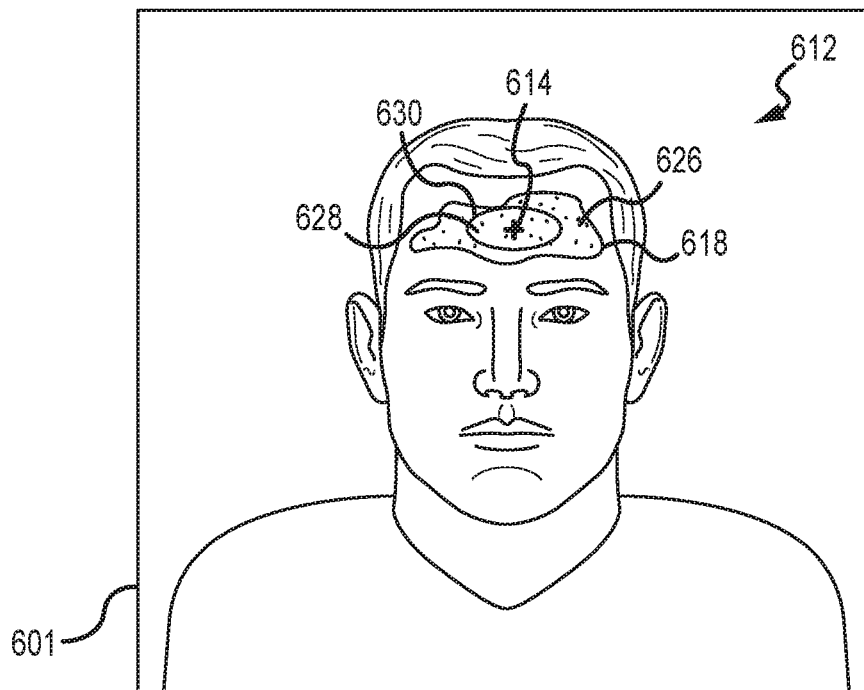
FIG. 6C depicts an image frame from a video signal, with a region of interest, according to an embodiment of the invention.

Another flood fill tool is illustrated in FIG. 6C. FIG. 6C shows a contiguous flood field 626, which spreads across the forehead until it reaches boundaries at the eyebrows and hairline. An optional approach is to identify a target region of interest (ROI) 628 within the contiguous region 626. The ROI 628 is fully contained within the contiguous region and excludes a portion of the contiguous region 626. The ROI is chosen as a region of anatomical interest, based on its location on the skin, and its likelihood of exhibiting a physiologic signal. The light intensity signal that is used to measure the patient's vital sign is then extracted from the ROI 628, rather than from the entire flood fill region 626. The ROI 628 is defined by its own boundary, such as an ellipse 630, to limit the size of the target region that is utilized for the vital sign measurement. The ellipse 630 defines a perimeter that excludes edges of the flood field 628 where pixels and boundaries can fluctuate more often than the pixels within the ellipse 630. The patient's vital sign is then measured from the ROI, where the pixels are relatively more stable and more likely to exhibit physiologic modulations with a suitable SNR. In an embodiment, the processor infers a size of the patient's forehead within the field of view and sizes the ellipse in proportion to the inferred size.

The size of the ellipse (or other shape) 630 can be chosen to provide a large enough number of pixels for a stable physiologic signal, but not so large as to degrade the SNR. Additionally, the ROI can limit the amount of computational power needed to process the extracted intensity signals, by excluding a portion of the contiguous region 626 and restricting the ROI to a manageable size. In an embodiment, if the contiguous region 626 is smaller than the ellipse, then the entire contiguous region 626 is used as the ROI. In an embodiment, the size of the ROI can be adjusted by a user or automatically suggested by the processor, increasing or decreasing the size of the ellipse (or other shape) 630, depending on the particular patient, skin tone, exposed skin area, initial calibrations, camera settings (such as color depth and dynamic range), lighting conditions, and processing power.

Although the boundary 630 is shown as an ellipse, other shapes may be used. For example, an elongated boundary (wider than it is high) is a good shape for the forehead. Other shapes can be used for other parts of the body, such as a circle (a type of ellipse) on the hand, or polygonal shapes. In an embodiment, the boundary of the ROI has a convex shape devoid of sharp corners. The ellipse 630 can be created by applying ratios from the face box 622 or the forehead location 624 of FIG. 6B. For example, the ellipse may be a proportion of the distance between the patient's eyes, or a proportion of the forehead region 624. The portion of the contiguous region 626 that is outside the boundary 630 is discarded, and the intensity signal is extracted from the ROI within the boundary 630, such as by averaging intensity signals from pixels within the ROI. In an embodiment, weighted averaging is employed, such as by weighting pixels near the center of the ROI more heavily than pixels near the boundary 630. In an embodiment, the weight is increased with increasing proximity to the center of the ROI.

Figure 7:
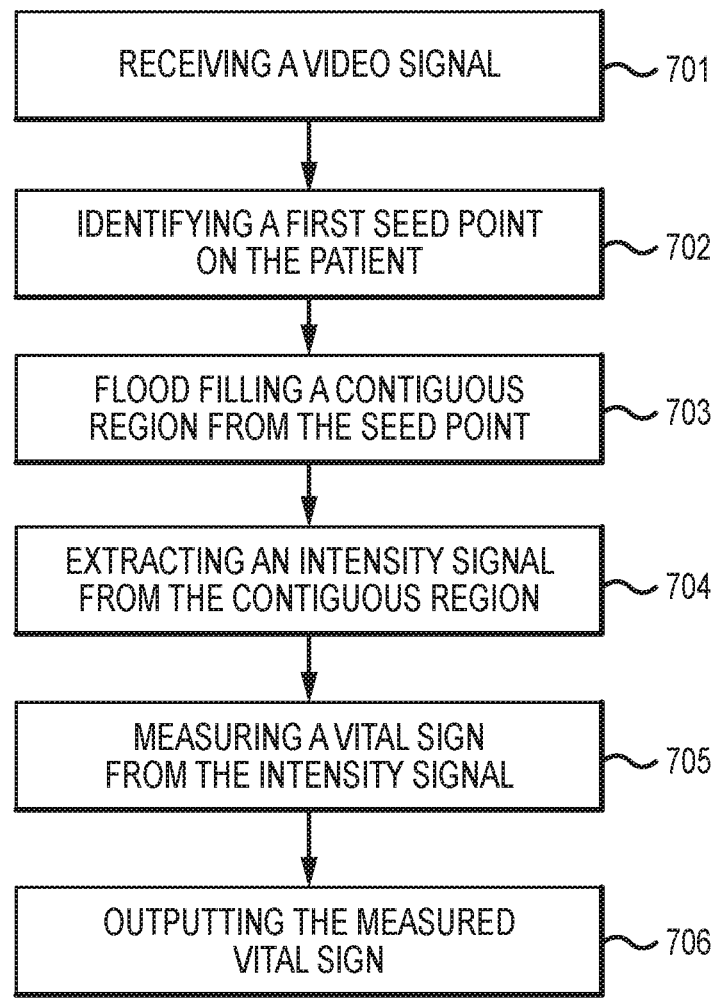
FIG. 7 is a flowchart of a method for video-based monitoring utilizing flood filling, according to an embodiment of the invention.

A method for video-based monitoring utilizing a flood fill method is outlined in FIG. 7. The method includes receiving, from a video camera, a video signal having a field of view exposed to a patient, at 701, and identifying a first seed point on the patient, at 702. The method includes flood filling a first contiguous region from the first seed point to a boundary, at 703, and extracting an intensity signal from the first contiguous region at 704. The method includes measuring a vital sign from the intensity signal at 705, and outputting the measured vital sign for further processing or display at 706.

Video photoplethysmogram signals acquired by flood fill filtering of a video signal from a patient are plotted in FIGS. 8A and 8B. Both figures show light intensity signals from the Green and Red channels from a video camera. Both the Green and Red signals exhibit amplitude modulations due to the patient's pulse rate, with the modulations in the Green signal exhibiting larger amplitude than the Red signal. FIG. 8A shows the signals over approximately 70 seconds, and FIG. 8B shows a zoomed in segment of 10 seconds. Both signals show some respiratory modulations, though they are more pronounced in the Green signal, appearing as shifts in the baseline or DC level of the signal.

Figure 9A:
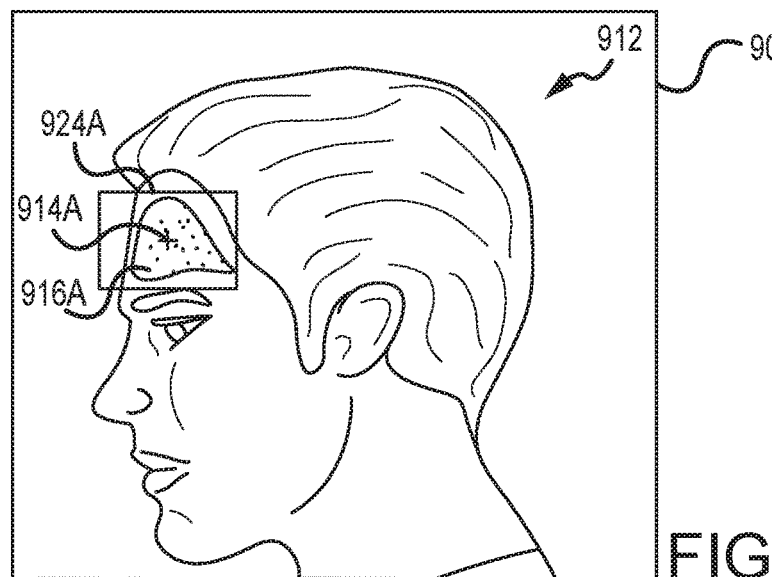
FIGS. 9A, 9B, and 9C depict image frames from a video signal, with a moving subject, according to an embodiment of the invention.
Figure 9B:
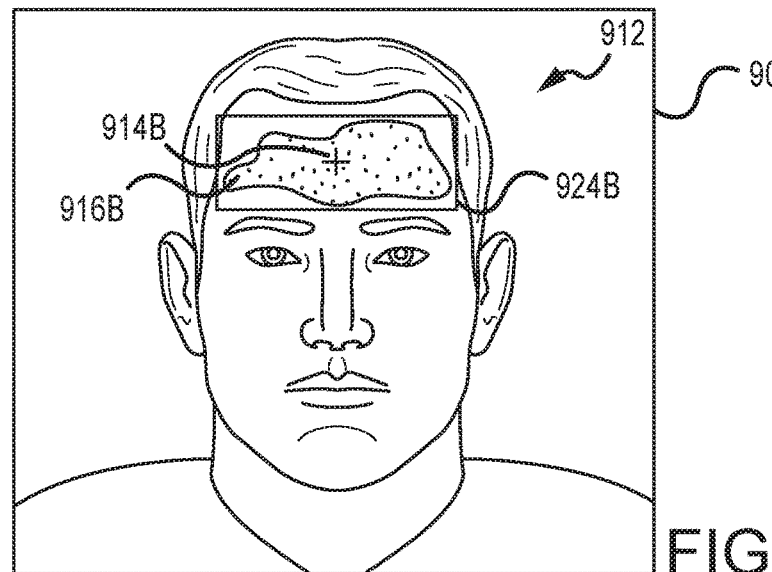
Figure 9C:
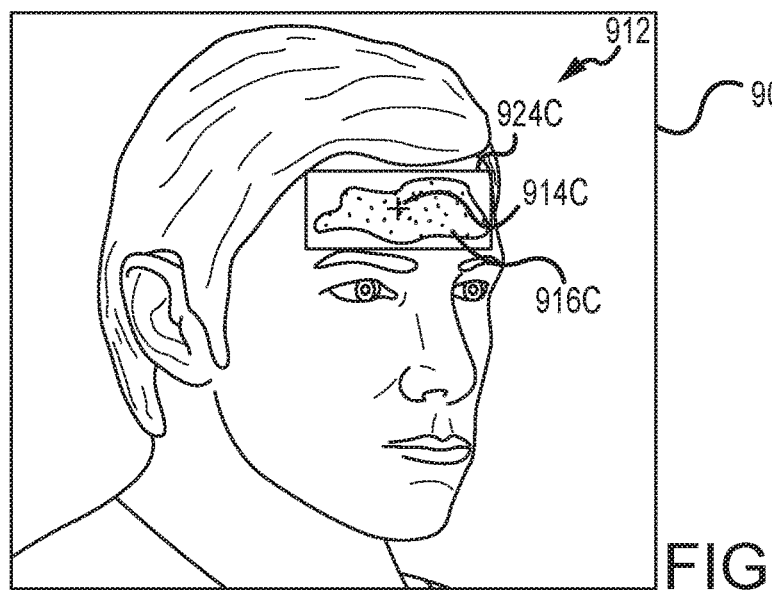

FIGS. 9A-9C illustrate an embodiment in which the flood fill region 916 dynamically changes over time to track movement of a patient 912 within the field of view 901. These figures show movement of the patient's head and torso, from facing down and to the reader's left in FIG. 9A, to a position facing straight toward the camera in FIG. 9B, to a position looking to the reader's right in FIG. 9C. The flood field 916 dynamically updates over time as the patient moves. In an embodiment, the seed point 914 is continually tracked, and the flood field continually updated to create a dynamically morphing contiguous region. The facial recognition tool identifies a forehead box 924 and places a seed point 914 inside the box. The flood field is then filled out from the seed point 914 until it reaches a boundary defining the flood field 916. These steps are repeated as the patient moves. In FIG. 9A, the processor has identified the forehead box 924A, assigned the seed point 914A in the middle of the box 924A, and flooded the flood field 916A around the seed point. The intensity signal for vital sign measurement is extracted from this flood field 916A (or from a sub-region within this flood field, as discussed with respect to the ellipse 630 in FIG. 6C). In FIG. 9B, the processor has tracked the patient's movement, moving the forehead box to its position at 924B, and re-assigning the seed point 914B to the middle of the forehead box, and re-generating the flood field 916B around the seed point 914B. In FIG. 9C, the processor has again tracked movement to the new position of the forehead box at 924C, re-assigned the seed point to the middle of the box at location 914C, and re-generated the flood field 916C. In an embodiment, the seeding position is updated with every frame; this may be referred to as the seeding frequency. A fast seeding frequency is useful for tracking motion, but may cause the seed position to jump erratically, in which case some temporal filtering can be applied.

This dynamic updating of the flood field (or the ROI within the flood field) enables tracking of the patient's physiological areas of interest during patient movement. Updating can be done with a static seed or a dynamic seed. A static seed is placed in a static location within an area, such as in the middle of a face box or forehead box or forehead ellipse (or other region or shape). If the static seed is obscured or moves out of view, the processor waits to regenerate the flood field until the static seed returns to view. Once the static seed is available again, the processor will generate the flood field from there again. A dynamic seed moves its location relative to a defined area like a forehead box or ellipse. For example, in an embodiment, the seed position is dynamically updated every frame by computing the centroid of the field and feeding it back into the flood fill method. The centroid of the new flood field is calculated, the seed point is moved to that centroid point, and then the process is repeated as each new flood field is generated.

In an embodiment, a new flood field is generated with each new seed point, and the flood field is then added to a running average to create a time-averaged flood field shape.

In an embodiment, the ROI is selected from this time-averaged shape, and the physiologic parameter is then calculated from the ROI. In an embodiment, a new flood field is generated upon a set seeding frequency, an adjustable seeding frequency, or upon a detected event, such as motion of the patient.

If the entire flood fill region rotates or moves out of view, the seed point is lost and the processor attempts to locate the patient within the field of view. In the meantime, the processor starts a timer that counts down and triggers an alarm if the timer expires prior to the seed point and ROI being re-established. A message may be displayed on a monitor screen while the timer is running, to alert a clinician that the processor is searching for the physiologic region within the image. When the patient is recognized, such as when the patient returns into the image or stops moving, the processor begins the process again, looking for anatomical features (such as facial recognition), assigning a seed point, and generating the flood field (and resetting the timer).

In an embodiment, the system is continually recognizing patient features and assigning a seed point, so that it can continually track movement of the patient within the field of view, and, if the patient exits the field of view, can resume tracking when the patient returns to the field of view. Further, movement of the seed point (or flood fill region, or ROI) across the field of view can itself be tracked as a motion signal, indicating that the patient is moving. This information can be useful to a clinician to put other vital signs in context, or to confirm that the patient is active (such as with neonates at risk of SIDS). In an embodiment, movement or variability of the seed point can be used as a criterion for validating that the seed point is located on the subject. For example, if the seed point lacks any movement or variability in location from frame to frame, and if the extracted intensity signal lacks a physiologic modulation, then the processor can reject the seed point as being located on a non-physiologic object, such as a photograph in the field of view. This variability criterion can be applied before displaying a vital sign.

If the seed point or ROI moves out of the image or is lost, the processor may also engage back-up or alternative methods as it attempts to re-locate the patient. For example, the processor may initiate a skin tone filter method (described in more detail below) to try to identify an area of skin in the image frame. If the skin tone filter identifies a candidate region, the processor may measure a physiologic parameter from that candidate region (or a portion of it) and output that physiologic parameter, even while it is still continuing to look for a seed point to re-establish a flood fill region.

In an embodiment, two different flood-filled contiguous regions are each used to extract the same or a different vital sign. For example, in FIG. 6A, the first seed point 614 on the patient's forehead is used to generate the flood field 616, from which the patient's pulse rate is measured. A second seed point 640 on the patient's ear is also identified, and is used to generate a second flood field 642, from which the patient's respiration rate is measured. As discussed above with respect to FIGS. 5A and 5B, different ROI's at different locations on the patient exhibit the same vital signs in different ways, such as one region exhibiting respiration rate more strongly than another. A second seed point can be chosen for the purpose of tracking respiration rate, or SpO2, or other vital signs. For respiration rate, a region along a border (such as the ear) can provide a signal with a good SNR.

In an embodiment, two or more different flood-filled regions are used to produce a single vital sign. The vital sign can be calculated from the first region and again from the second region, and then the two calculated values can be averaged together to produce an output vital sign measurement. In an embodiment, the averaging is weighted, based on signal quality or anatomical preference. For example, the vital sign calculation from the forehead region can be weighted heavier than the vital sign calculation from the cheek region, given that the forehead tends to be better perfused than the cheeks. In an embodiment, forehead SpO2 is calculated from a forehead flood fill region, and cheek SpO2 is calculated from a cheek region, and the forehead SpO2 and cheek SpO2 values are averaged into a final SpO2 value (which can itself be added to an averaging filter for display). In another embodiment, forehead respiration rate is calculated from a forehead flood fill region, and chest respiration rate is calculated from a chest region (which may or may not be flood filled), and those values are averaged into a final respiration rate value. The forehead, cheek, and chest are given as examples only and can vary in other embodiments.

In another embodiment, two different vital signs can be measured from two different portions of the same flood field. For example, referring to FIG. 6C, pulse rate can be measured from the ROI 628 inside the ellipse 630, and respiration rate can be measured from the remainder of the flood fill region 626, between the ellipse 630 and the boundary 618. In another approach, different vital signs can be measured from the same region (such as both from the same ROI 628) but based on different weighting of the pixels within that region. For example, a first light intensity signal can be generated from the ROI 628 by weighting the pixels more heavily toward the center of the ROI 628 (away from the ellipse 630), and a second light intensity signal can be generated from the ROI 628 by weighting the pixels more heavily away from the center (toward the ellipse 630). This can produce two different signal that behave similarly to those shown in FIGS. 5A and 5B, with one signal more strongly exhibiting a respiration modulation. As an example, the patient's pulse rate can be measured from the first signal, and respiration rate from the second.

Figure 10A:
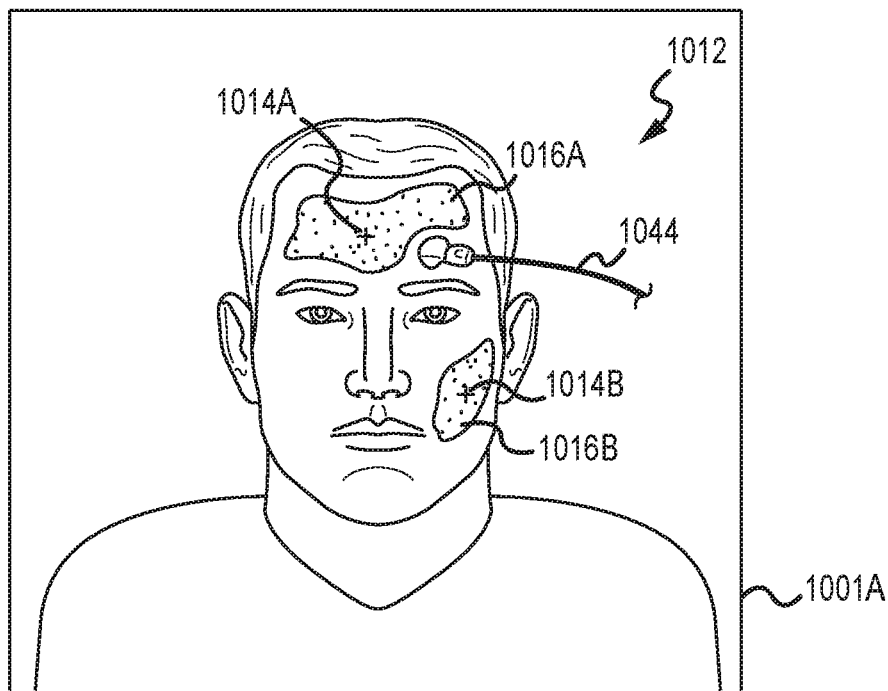
FIG. 10A depicts an image frame from a video signal, with multiple flood fill regions, according to an embodiment of the invention.

The flood fill approach is also useful in automatically excluding non-physiologic areas such as sensors and bandages, as illustrated in the embodiment of FIG. 10A. In FIG. 10A, a patient 1012 is wearing a sensor 1044 on the forehead, above the patient's left eyebrow. Based on facial recognition and/or user input, the system has identified two seed points 1014A and 1014B, and generated two flood fill regions 1016A, 1016B, respectively. The forehead region 1016A encounters the sensor 1044 and automatically excludes it from the region, based on different characteristics of the pixels along the sensor. The flood fill method automatically defines this boundary, excluding pixels that are less likely to contribute a physiologic signal.

Figure 10B:
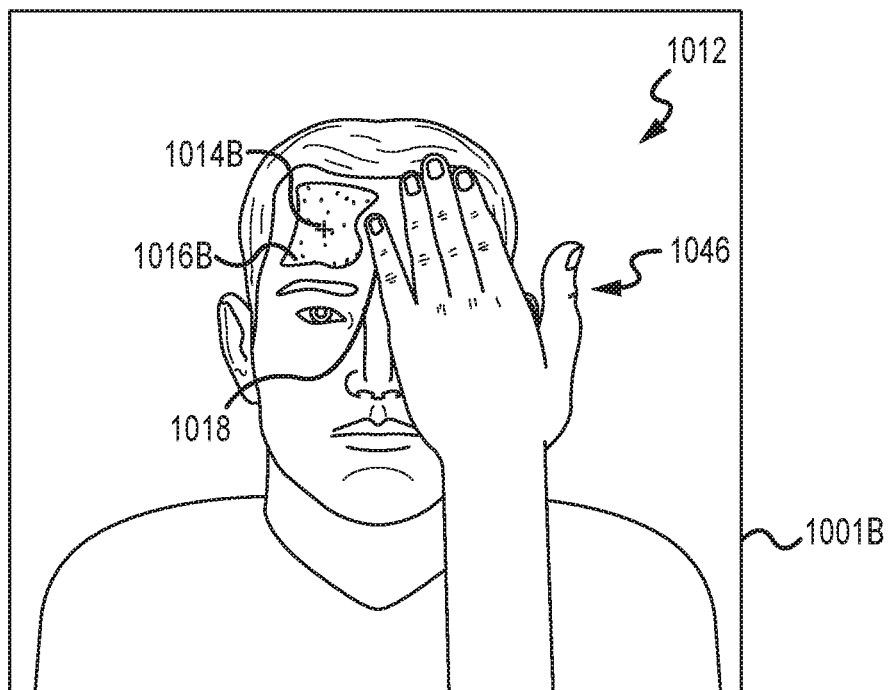
FIG. 10B depicts an image frame from a video signal, with an obscured region, according to an embodiment of the invention.

Dynamic updating of the flood fill region is also useful to exclude passing artifacts, as illustrated in the embodiment of FIG. 10B. In FIG. 10B, the patient 1012 is waving a hand 1046 across the field of view 1001, temporarily obscuring his or her face from the camera's view. With dynamic updating, the seed point 1014B automatically moves within the recognized area of the patient's face, and the flood fill region 1016B is automatically updated around the seed point 1014B. As the patient's hand (or other object) moves across his or her face, the flood fill region automatically shifts to avoid the passing artifact, by adjusting itself and refreshing the contiguous region that matches the desired characteristics around the seed point. In FIG. 10B, the contiguous region 1016B has shrunk and shifted to the reader's left, truncated at the new boundary 1018 presented by the side of the user's hand 1046. As the user's hand (or other object) continues moving across the face, the boundary 1018 continues to move and adjust, defining the contiguous area and excluding the hand (or other object) due to its different characteristics. When the hand (or other object) has finished passing by, and the patient's face is fully visible again, the flood fill region will again refresh based on the newly assigned seed point, enabling truly dynamic tracking and artifact rejection.

Figure 10C:
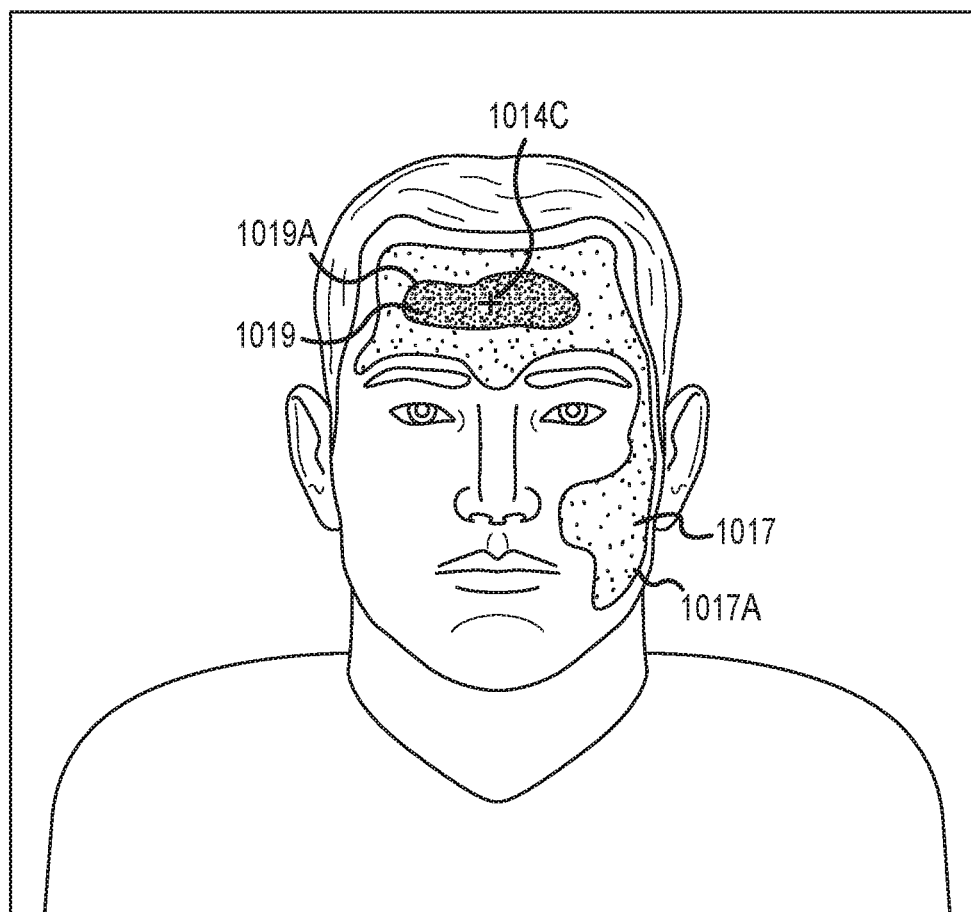
FIG. 10C depicts an image frame from a video signal, with overlapping flood fill regions, according to an embodiment of the invention.

Tolerances for the contiguous, flood filled region can be adjusted to expand or narrow the size of the region, as illustrated in the embodiment of FIG. 10C. In FIG. 10C, two flood filled regions 1017 and 1019 are generated from a single seed point 1014C. The region 1017 has wider tolerances than the region 1019. As a result, the region 1017 expands further across the patient's face, until reaching a boundary 1017A where neighboring areas no longer share the evaluated characteristics within the relatively wider tolerances. Meanwhile, the region 1019 stops at an earlier boundary 1019A, including a smaller area that shares characteristics within relatively narrower tolerances. Tolerances can be adjusted to generate flood filled regions of various sizes, and different physiologic signals can be measured from the different regions.

In an embodiment, the size of the flood fill region is monitored and used as an indication of confidence in the physiologic signal. In particular, the variability in the size of the region can be a useful indicator. If the patient is moving, or if lighting conditions are changing rapidly, or if an object is waving back and forth in front of the patient, then the flood fill region (such as region 1017 or 1019 in FIG. 10C) will change in size as it attempts to dynamically track the patient and fill a region from the seed point. In such a dynamic situation, the boundary (such as 1017A or 1019A) moves frequently to accept or reject neighboring pixels or areas, and the size and/or location of the flood fill region changes quickly. The size or location of the region can be calculated, and the variability of the size or location calculated over time. If the variability exceeds a threshold, the physiologic signals measured from the flood fill region can be flagged as having low confidence, and/or a confidence metric can be reduced, and/or an indicator or alarm can be triggered. This same approach can be used by tracking the location of the seed point—if the location changes rapidly, a low-confidence flag can be set and/or a confidence metric reduced. Conversely, if the size of the flood fill region and/or the location of the seed point are stable, then a confidence metric can be increased and/or a high-confidence flag set.

In an embodiment, the flood filled region is displayed to the user, such as a doctor, nurse, or clinician, so that the user can understand the basis for the physiologic signals and the measured vital signs, and can assess whether any action is needed, such as an input to change the seed point (described in further detail below), a change in lighting conditions in the room, increasing or decreasing the size of an ROI (such as ellipse 630), or other actions.

Figure 11:
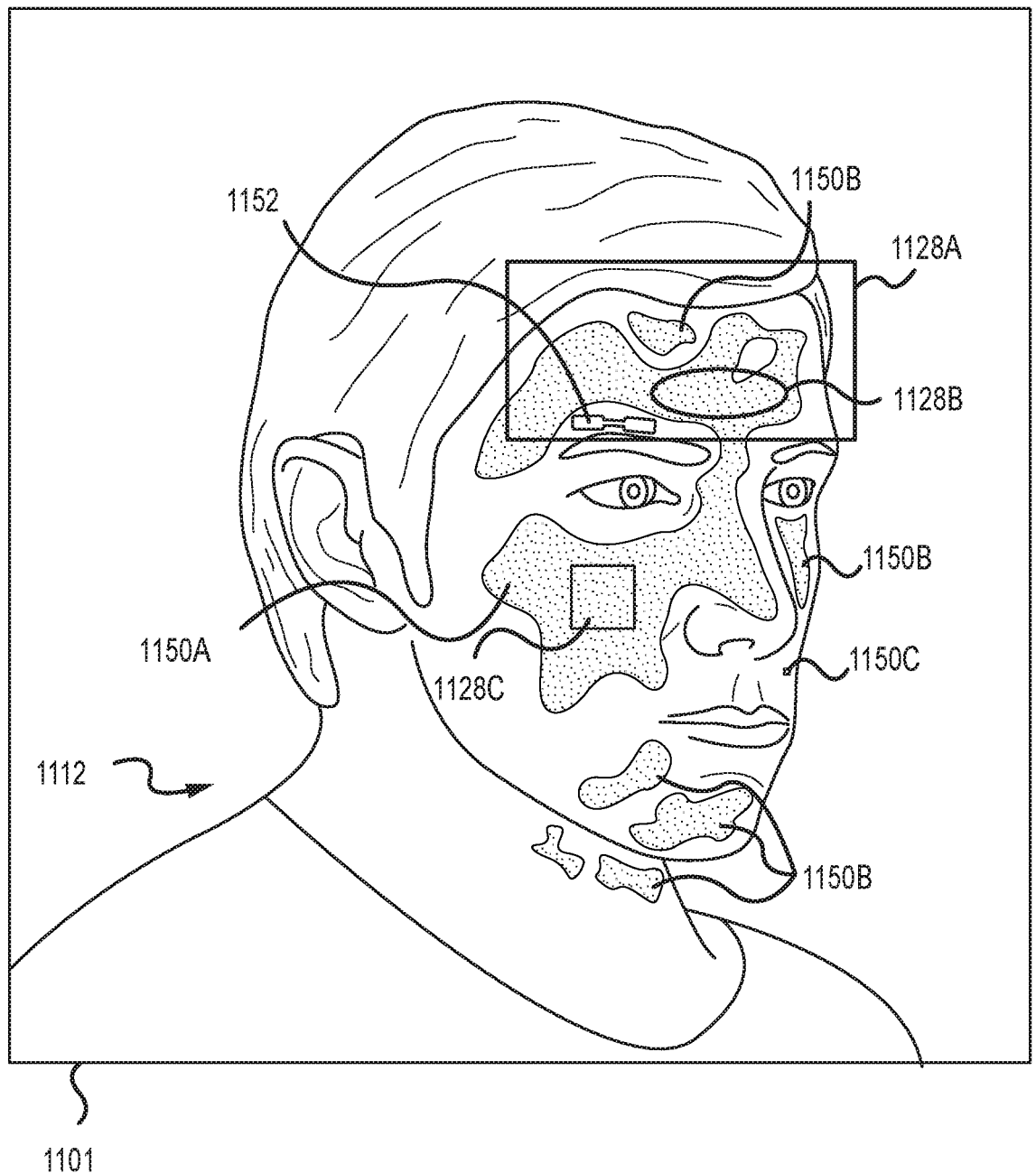
FIG. 11 depicts an image frame from a video signal, with skin tone filtering, according to an embodiment of the invention.

In an embodiment, a skin filtering method is employed in order to recognize a physiologically relevant portion of an image frame. An example image frame 1101 is shown in FIG. 11. In this method, a skin tone filter identifies candidate skin pixels, and light intensity signals are extracted from candidate skin pixels within target regions or regions of interest (ROI's) on the patient. A skin tone filter operates by identifying pixels that fall within a range of color values. This range of color values includes those colors that are likely to be reflected from the subject's skin. The particular range of color values for an individual patient depends on the patient, the medical situation, and ambient light conditions. Approaches for setting the target range of color values are discussed in more detail below. The skin tone filter evaluates pixels within the image frame (or a designated portion of the image frame) and identifies those pixels that have color values that fall within the target range. Skin tone filtering finds these pixels anywhere in the image frame, as contrasted from flood fill, which finds pixels that are spatially connected to each other.

FIG. 11 shows an image frame 1101 with a patient 1112. The image frame 1101 is passed through a skin tone filter to identify candidate regions 1150A-C, which are shaded in FIG. 11. The candidate regions include identified skin pixels that may be spread across the image, in some large groups (such as 1150A) and some smaller groups (such as 1150B) or even individual pixels (such as pixel 1150C). The candidate region is not necessarily contained in one single, contiguous region. In an embodiment, the skin tone filter refreshes continually, or at a periodic frequency such as once per second, to identify the candidate regions 1150 as they may change over time, such as when the patient moves, lighting conditions in the room change, or items such as a bandage 1152 are placed over the patient's skin, obscuring some of the skin from the camera's view. The skin filter refreshes so that it tracks the patient in the image and continues to identify candidate areas for measurement of physiologic signals.

In an embodiment, a light intensity signal is extracted from all of the candidate regions 1150 that are passed by the skin tone filter. Vital signs such as pulse rate, respiration rate, and SpO2 can be measured from the extracted intensity signal, as discussed above. In another embodiment, the candidate regions are further sub-divided and selected before the physiologic vital signs are measured. For example, in an embodiment, a target region of interest (ROI) is identified on the patient, and the light intensity signal is extracted from the pixels with that ROI. Three non-overlapping ROI's 1128A, 1128B, and 1128C are shown in FIG. 11 (though in other embodiments they may overlap). The ROI 1128A is a forehead box which can be automatically configured and placed by facial recognition tools. The ROI 1128B is a smaller ellipse within the forehead box. The ROI 1128C is a region of the cheek, which can also be configured and placed by facial recognition tools, including by creating a box that is a determined ratio of the forehead box, and placing it a determined distance below the forehead box. A light intensity signal is then extracted from the skin-tone filtered pixels within each ROI. In an embodiment, the light intensity signal from a skin tone filtered area or a particular ROI with skin-tone filtered pixels is first checked for physiologic modulations, to make sure that the area it is viewing is physiologic. If the area lacks physiologic variability (such as a modulation at an expected hear rate), it can be rejected as being located on a non-physiologic object, such as a photograph in the field of view, and the algorithm can look for or ask for a new seed point for flood filling or new color ranges for skin tone filtering. The skin tone filtering method is useful in this regard, as the entire image can be scanned to find pulsating, physiologic portions of the image, without any prior knowledge of what is within the field of view. For example, the skin tone filter can identify areas of exposed skin for extraction of a physiologic signal, without having to first recognize facial features or identify a seed point.

Figure 12A:
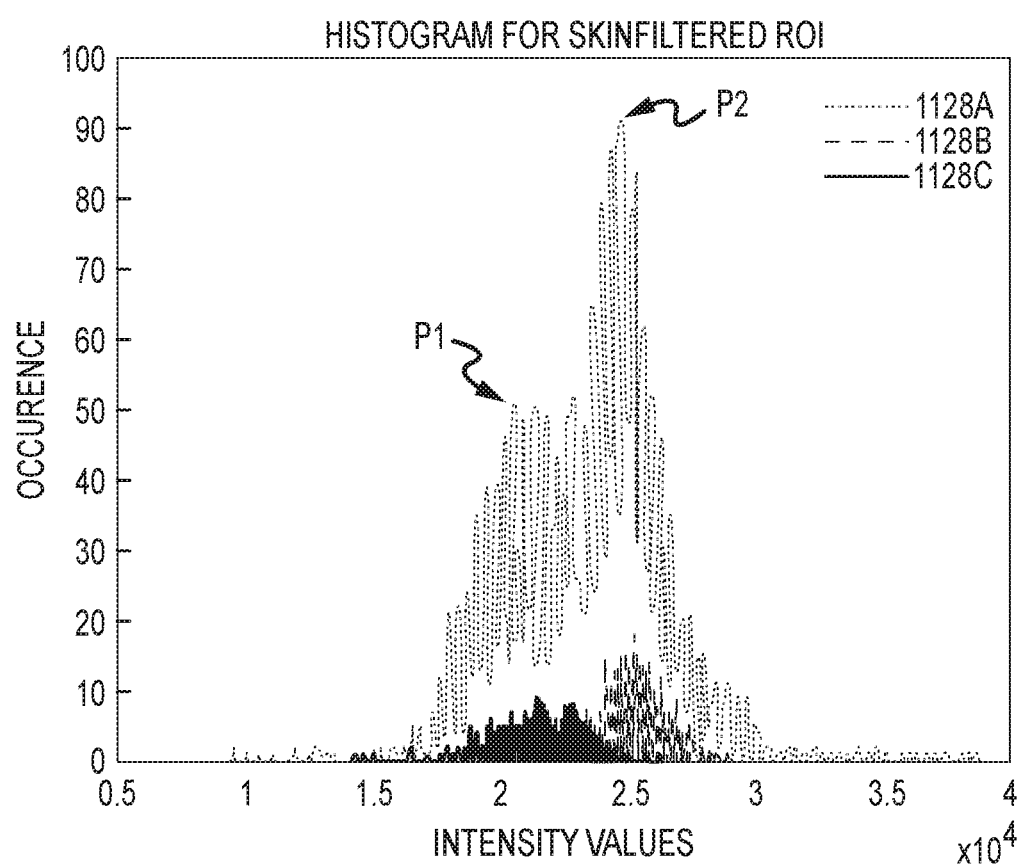
FIG. 12A is a histogram of intensity values from FIG. 11, according to an embodiment of the invention.

In an embodiment, one of several ROI's is chosen for physiologic measurement based on desired characteristics of the intensity signal extracted from that ROI. For example, the intensity signals extracted from each of ROI's 1128A, 1128B, and 1128C are plotted in a histogram in FIG. 12A. This histogram is taken from a snapshot of the intensity signals, and shows the number of pixels within each ROI (y-axis) that exhibited each intensity value (x-axis). The intensity value can be taken from a single channel (such as Red, Green, or Blue), or an average or sum of the channels, a greyscale intensity value, or another value representative of pixel intensity. The forehead ellipse 1128B and the cheek region 1128C both exhibit a uni-modal intensity distribution—a histogram distribution with a single peak (shown in the lower part of the histogram). By contrast, the larger forehead box 1128A exhibits a bi-modal intensity distribution, with two distinctive peaks noted at P1 and P2 in FIG. 12A. In an embodiment, the ROI that is selected for physiologic measurement exhibits a uni-modal distribution.

In an embodiment, an ROI that exhibits a bi-modal or multi-modal distribution is discarded or down-weighted. This approach has been found to improve the stability and strength of the physiologic signals extracted from the selected ROI. For example, a bi-modal distribution may be caused by two groups of candidate skin pixels within an ROI, one for each peak in the distribution, with one group being closer to a light source or closer to an edge of an anatomical feature than the other group. If the patient moves or the lighting conditions in the room change, one of those two groups may be eliminated the next time the skin tone filter refreshes, causing the ROI to suddenly shift its intensity distribution toward the other, remaining group of pixels. This shift in pixels causes a corresponding shift in the extracted intensity signal, which can temporarily obscure the underlying physiologic signal. Later, when the patient moves again or the lights return to a previous setting, the second group of pixels may re-appear in the ROI, causing another shift in the signal. As a result, ROI's with bi- or multi-modal intensity distributions may suffer from a lower SNR or more variability than uni-modal ROI's.

In another embodiment, a bi- or multi-modal ROI is not discarded but is monitored separately. If the distribution remains bi- or multi-modal over a period of time, the ROI may be used for vital sign measurement. If the distribution alternates between uni-modal and bi-/multi-modal (or between number of modes), then the ROI may be ignored until its distribution becomes more stable. In an embodiment, a bi- or multi-modal ROI is deconstructed into individual uni-modal distributions, and the intensity range of one of these individual distributions is then used to identify a corresponding ROI in the image (such as by feeding that intensity range into the skin tone filter). Two or multiple uni-modal ROI's can thus be produced from the bi- or multi-modal distribution. These uni-modal distributions can be tracked and analyzed for vital sign measurement, though one or more of them may disappear due to motion or changes in lighting.

In an embodiment, ROI's with bi- or multi-modal intensity distributions may be discarded, and of the remaining ROI's (which have a uni-modal distribution), one ROI is chosen for physiologic measurement. The larger the ROI, generally the better the SNR due to the averaging effects of the pulse amplitudes of the pleth. SNR of the pleth is generally measured as ratio of the amplitude of the pleth against the background noise, which is obtained from a non-skin region. In an embodiment, the largest ROI is chosen. In another embodiment, the ROI with the strongest SNR is chosen. In another embodiment, the largest or most stable forehead region is chosen as the ROI. This can be based on choosing the peak surface intensity in the ROI.

Peak surface intensity will be dependent on individual subject characteristics. For example if subject has a bump on the forehead due to swelling compared to a normal section of the forehead, the bump would tend to have a peaked surface compared to the normal region of the forehead.

Figure 12B:
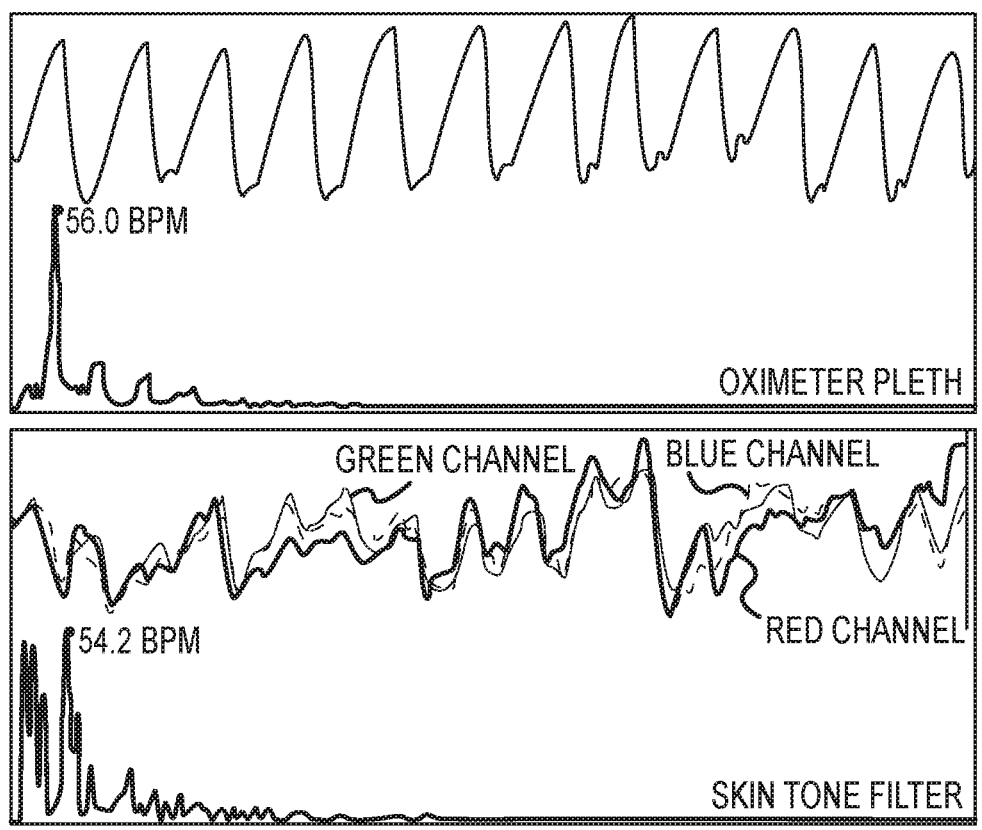
FIG. 12B is a chart of intensity values from a video signal (bottom) and a reference photoplethysmogram from an oximeter (top), and a corresponding frequency transform for each, according to an embodiment of the invention.

FIG. 12B shows the light intensity signals (Red, Green, and Blue) extracted from a forehead ROI such as 1128B from FIG. 11, next to a signal from a conventional contact-based pulse oximeter, for reference. The reference pulse oximeter shows a pulse rate of 56.0 bpm (taken from an FFT of the oximeter PPG signal), while the video-based light intensity signal shows a pulse rate of 54.2 bpm (taken from the average of the FFT peaks of the three R, G, and B signals from the video).

Figure 13:
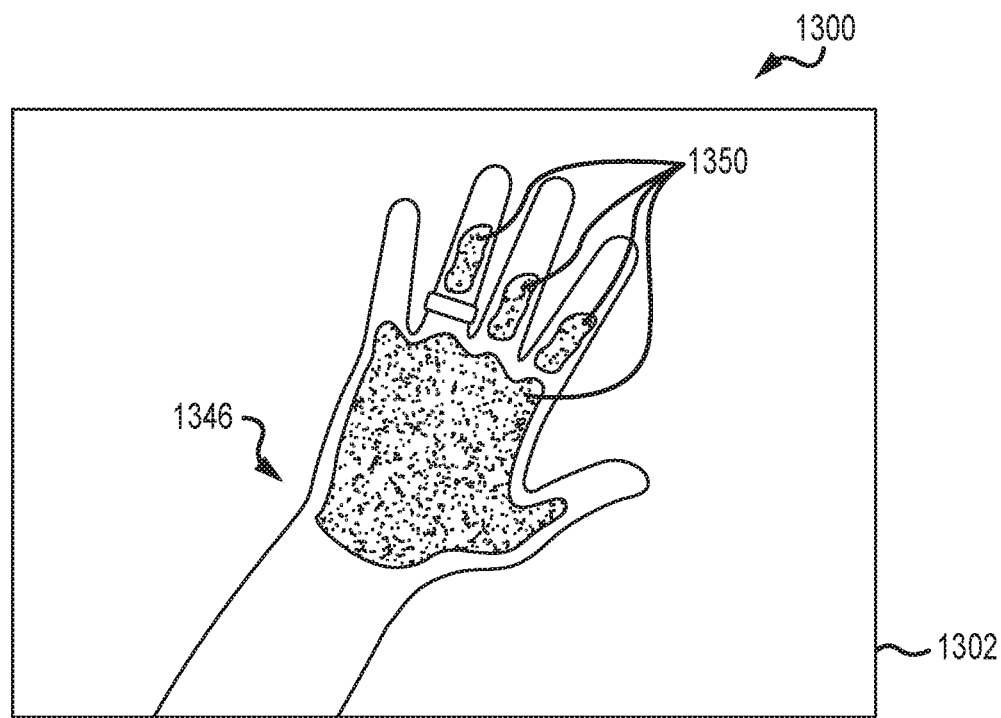
FIG. 13 depicts an image frame from a video signal in view of a hand, according to an embodiment of the invention.

Skin tone filtering can be applied to detect any area of exposed skin, including the face, torso, hands, feet, arms, and legs. An image frame 1300, shown in FIG. 13, views a field of view 1302 exposed to a hand 1346. A skin tone filter is applied to the image to identify candidate skin pixels 1350. A light intensity signal can be extracted from all of these pixels 1350, or from a smaller ROI, and the patient's vital signs can be measured from the extracted intensity signal, as described above.

Figure 14:
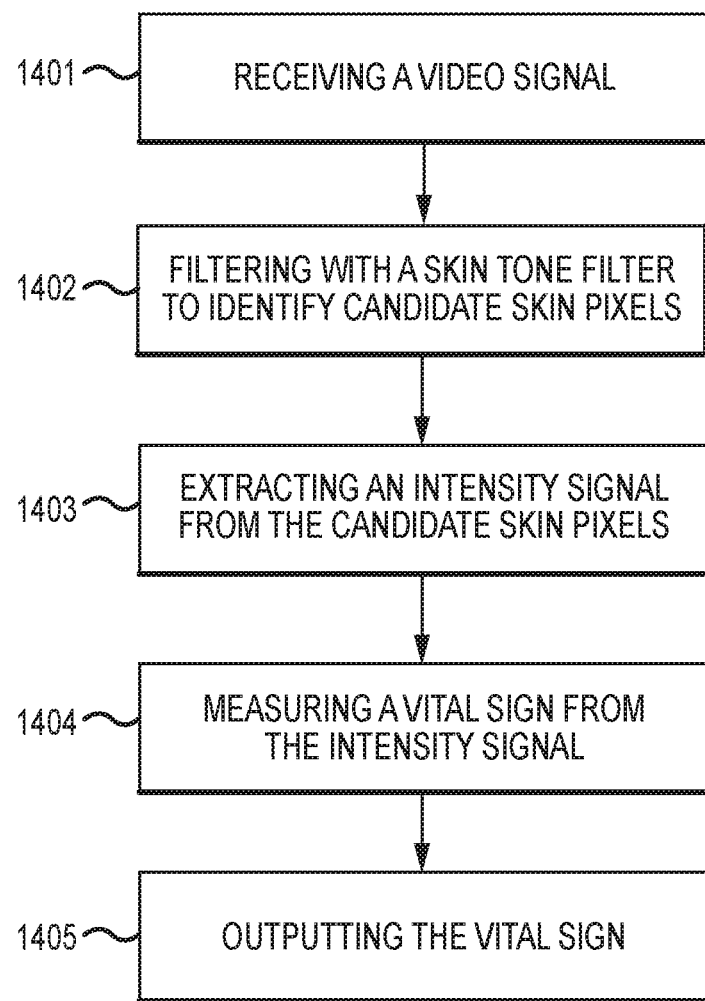
FIG. 14 is a flowchart of a method for measuring physiologic parameters from a video signal using a skin tone filter, according to an embodiment of the invention.

A method for measuring physiologic parameters from a video signal using a skin tone filter is shown in FIG. 14. In an embodiment, the method includes receiving, from a video camera, a video signal encompassing exposed skin of a patient, at 1401, and filtering the video signal with a skin tone filter to identify candidate skin pixels within the video at 1402. The method includes extracting an intensity signal from the candidate skin pixels at 1403. The method includes measuring a vital sign from the intensity signal at 1404, and outputting the vital sign for further processing or display at 1405. In other embodiments, one or more ROI's can be identified prior to skin tone filtering, and the skin tone filter can be applied within those ROI's. Then intensity signals can be extracted from the identified pixels in each ROI, and one or more extracted intensity signals can be selected or combined, and then the vital sign measured. In another embodiment, one or more ROI's can be identified after skin tone filtering, and the candidate skin pixels within that ROI used to extract the intensity signal.

The skin tone filter utilizes a range of color values, passing those pixels that are within the range. Several options exist for setting this range. In an embodiment, a user, such as a doctor or nurse, provides an input that identifies an area of the patient's skin, such as by tapping on a touch screen, or clicking with a mouse, on the patient's forehead, face, hand, or other area of skin that is exposed in the image. The processor then stores the color values of the pixels in that area, generates a tolerance range around those color values, and uses that range for the skin tone filter. The tolerance range depends on skintone, color space and color depth of the images, and even the level of illumination (i.e. global brightness). Example ranges in the RGB color space (global range 0-255) include R:92-131 G:114-154 B:159-201 (for lighter skin tones), and (R:40-79 G:67-106 B:95-126) (for darker skin tones). These tolerances can be set in other color spaces, such as HSV. In another embodiment, the processor employs facial recognition tools to identify the patient's face, picks a seed point within the patient's forehead (or other region), and develops the range of color values from the seed point. The initial seed point can also be marked as a preferred point based on initial calibration or input by a user (physician, nurse, or other attending staff) (as described below with reference to FIGS. 15A-D). Then seeding can be combined with facial recognition and tracking, in order to select the preferred seeding point.

In another embodiment, after a seed point is identified (whether by the user tapping or clicking, or the processor selecting a point), a contiguous region is flooded from that seed point, using a flood fill method as described above. Once the contiguous region is filled, the range of color values within that contiguous region is then evaluated and set as the range for the skin tone filter. For example, the system identifies intensity values of the pixels in the flooded contiguous region (such as a histogram of Red, Green, and Blue values) over a short calibration time period. Then the range for the skin tone filter is set around those identified values (such as a percentage, 95% or other, of the values in the histogram). A suitable amount of time for the calibration time period includes three or more cardiac pulses, to include the range of intensities due to the physiologic pulse.

The skin tone filter then processes the image and identifies all the candidate skin pixels, whether or not contiguous and whether or not within the filled region. The candidate skin pixels, or a sub-set of them, form the target region. An intensity signal is extracted from the target region, and vital signs calculated from that signal. This approach is useful for tracking an ROI through changing lighting conditions. Over the course of a day, the lighting conditions in a room may change such that the light reflected from a patient's skin is within one range of color values at one time, and a completely different range of color values at a later time. The processor can track the seed point and continue to flood fill a region from the seed point, based on the characteristics of that seed point, through changes in lighting. Then, the range of color values from the flood filled area is input into the skin tone filter so that the skin tone filter can refresh its identification of areas throughout the image that are candidate skin areas. This combination of flood fill and skin tone filtering addresses the difficulty in identifying appropriate skin tone ranges across various lighting, patient, and environmental conditions.

In another embodiment, a seed point is not identified, but rather the skin tone filter iterates through several possible range of color values, based on the range of values that is likely to be reflected from a patient's skin. The range that results in the most candidate skin pixels within an ROI, or that results in a light intensity signal with the highest SNR, is then chosen as the range for the skin tone filter. The possible ranges for this exercise may be pre-programmed in the processor, or may be determined by reference to a color or greyscale card or graphic that includes likely skin tones and that is placed in the field of view. The processor can then identify the range of color values reflected from that card and iterate through those ranges with the skin tone filter.

In an embodiment, a first PPG signal is extracted from a contiguous flood-fill region and a second PPG signal is extracted from a skin-tone filtered region. The two PPG signals can be combined together (such as an average or weighted average) into a combined PPG signal from which to measure a vital sign, or one of the two signals can be selected based on quality criteria. In an embodiment, a vital sign is measured separately from each PPG, producing a flood-fill vital sign measurement and a skin-tone-filter vital sign measurement, and the measurement that appears to be the most reliable is chosen, based on quality, SNR, variability, and similar criteria. In an embodiment, the skin tone filter PPG is analyzed first, and a vital sign such as pulse rate is calculated from the skin tone filter PPG. If that measurement fails for any reason, then the flood fill PPG is used as a second, backup option for determining the vital sign.

In an embodiment, the skin tone filter dynamically updates over time, continually refreshing to identify the candidate skin pixels in the changing video stream. In an embodiment, an initial calibration period is utilized first, to determine initial parameters for the skin tone filter, and to map the face (including noting differences such as bandages, sensors, etc on the face). After that initial calibration, the skin tone filter dynamically updates as the environment changes (subject to a maximum refresh rate), or at a set frequency such as once per second or faster.

Figure 15A:
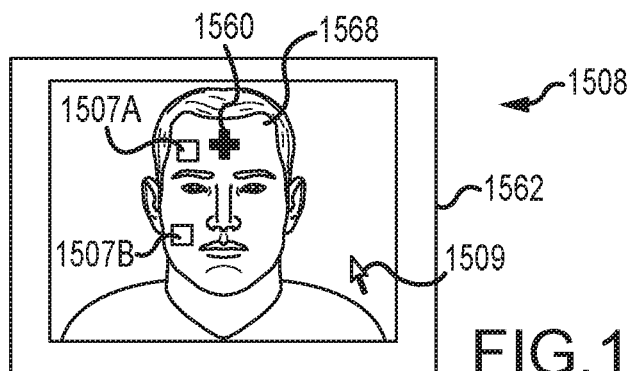
FIG. 15A is a display screen depicting user inputs, according to an embodiment of the invention.

In an embodiment, a processor accepts a user input to assist the processor in identifying relevant areas of the patient in the image. A few examples are shown in FIGS. 15A-D. For example, in FIG. 15A, a user touches (on a touch screen) or clicks (on a mouse) at location 1560 to locate an area of the patient on a display screen 1562 (which may be a touch screen). In FIG. 15A, the input location 1560 corresponds to a location on the patient's forehead 1568. The processor can then use this location 1560, or a nearby location on the forehead 1568, as a seed point for a flood filling method, for skin tone filtering, for facial recognition, or for defining an ROI, as discussed above. The input can be a click from a mouse or a touch input (such as a gesture or tap) on a touch screen, or a confirmation entered on a keyboard.

In an embodiment, the input can be performed remotely by a physician, as part of a remote non-contact monitoring system. The input may be performed on a still image of the patient from the video stream, or from the live video stream. For example, any of the images in FIGS. 15A-D can be a still shot, frozen from the live video stream, in which case the input from the user is taken by the processor and applied to the live video stream. If environmental or patient conditions have changed drastically in the interim (which could be only a few seconds), then the processor may need to prompt the user to try again; however, if conditions have not changed much, then the processor can apply the input from the frozen shot to the live video. Alternatively, any of the images in FIGS. 15A-D can be a live video stream, and the user provides the input in real-time. The input can be a point on the face, forehead, nose, cheek, hand, shoulder, chest, eyes, or other anatomical area of the patient. The processor can infer other relevant areas in spatial relation to the user input, such as placing a forehead box above the eyes, or placing a face box centered on the nose.

Figure 15B:
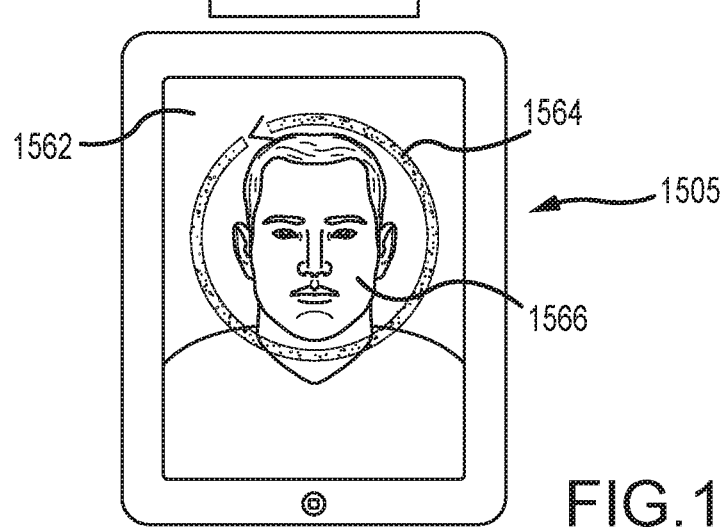
FIG. 15B is a hand-held display (such as a tablet or smart phone) depicting user inputs, according to an embodiment of the invention.

In FIG. 15B, the user inputs a gesture 1564 on the touch screen 1562. The gesture 1564 involves swiping or circling to locate an area 1566 of the patient. In FIG. 15B, the user has swiped or circled around the patient's face 1566 to identify the location of the face in the video signal. The processor can then identify a seed point within the located area. The gesture 1564 need not be fully enclosed and may be an open circle, or may include some areas around the patients face. The processor can employ facial recognition tools to find relevant areas of the patient based on the initial location or region provided by the gesture 1564. In FIG. 15B, this gesture 1564 is performed on a hand-held device 1505 such as a tablet, smartphone, or similar device.

Figure 15C:
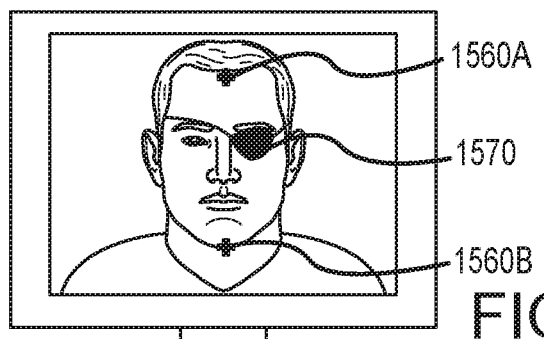
FIG. 15C is a display screen depicting user inputs, according to an embodiment of the invention.

In FIG. 15C, the user inputs two locations 1560A and 1560B near opposite ends of an anatomical feature of the patient, such as at the top and bottom of the patient's face. The processor then focuses on the area between the locations 1560A and 1560B for facial recognition. This user input can help the processor find facial features even when they are partially obscured, such as by the eye patch 1570 in FIG. 15C.

Figure 15D:
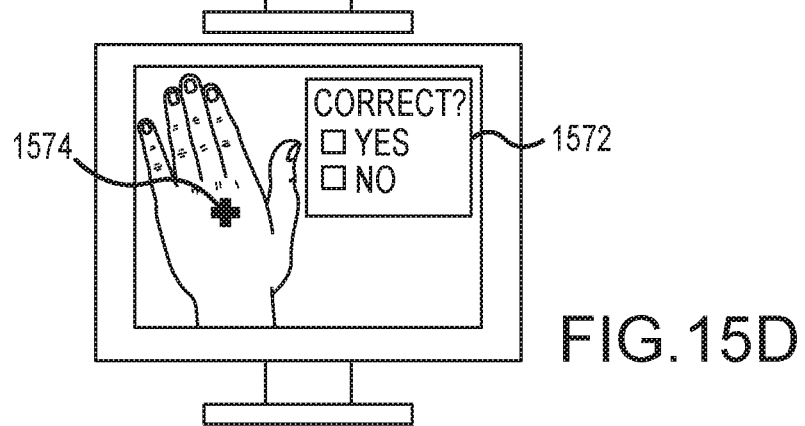
FIG. 15D is a display screen depicting user inputs, according to an embodiment of the invention.

In FIG. 15D, the processor outputs a suggested seed point 1574 and a prompt 1572 to the user to confirm that the suggested seed point 1574 is correct, meaning that it does fall on a relevant area of the patient, such as exposed skin, or an anatomical feature. The user clicks, touches, or otherwise selects "Yes" or "No" to inform the processor whether to proceed with point 1574 or pick a different point. In another embodiment, the processor outputs a prompt to ask the user to locate a requested area on the patient, such as asking the user to click or tap on the patient's face, forehead, or other location. In an embodiment, the processor recognizes a facial feature of the patient, prompts the user to confirm, and in response to the confirmation, identifies a seed point on the patient in spatial relation to the recognized facial feature, and flood fills a contiguous region from the seed point. In another embodiment, the user swipes around the patient's face, and then the processor identifies a face area within the image, determines a range of color values for a skin tone filter, and then skin tone filters the image (or just the face area) to identify candidate skin pixels for further processing. Other combinations of swipes, clicks, and taps can be used, such as a click-and-drag input where the user clicks (or taps) at the location of the seed point, and then drags the finger or curser away to expand the flood field out from the seed point. By dragging farther, the user is creating a larger flood field, with looser tolerances, and by dragging back in toward the seed point, the user is creating a smaller flood field, with tighter tolerances. The result can be shown to the user in realtime on the display, and the user releases the drag when satisfied with the resulting flood field.

In an embodiment, the processor outputs a prompt, asking the user to identify a location on the patient, in response to a determination of low or no confidence in an automated facial recognition. For example, the system may at first attempt to recognize a face within the image, and if it fails or has low confidence in the result, it then outputs a prompt to the user to locate an area of the patient in the image.

Figure 16:
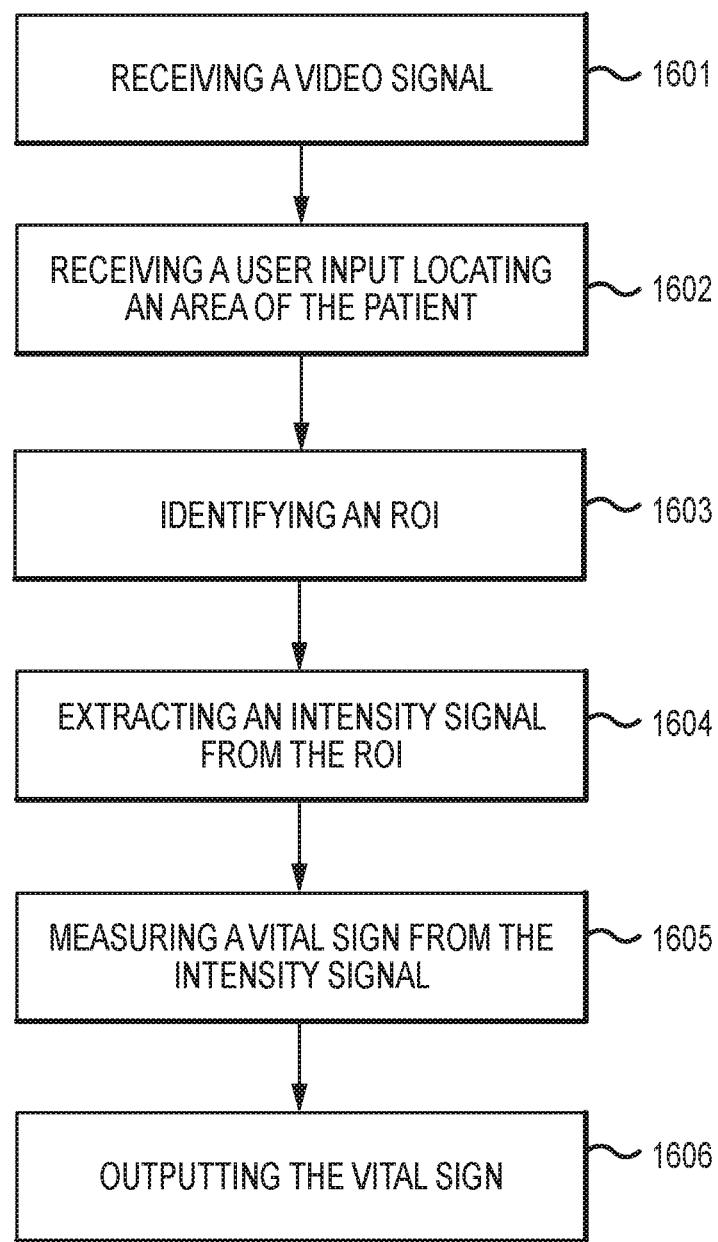
FIG. 16 is a flowchart of a method for measuring a patient's vital sign from a video signal, with a user input, according to an embodiment of the invention.

A method for measuring a patient's vital sign from a video signal, with a user input locating an area of the patient, is outlined in FIG. 16. In an embodiment, the method includes receiving, from a video camera, a video signal having a field of view exposed to a patient at 1601, and receiving, from a touch screen, keyboard, or mouse, a user input locating an area of the patient at 1602. The method includes identifying, with a processor, a region of interest in the located area at 1603 (such as by flood filling or skin tone filtering) and extracting an intensity signal from the region of interest at 1604. The method includes measuring a vital sign from the intensity signal at 1605 and outputting the vital sign for further processing or display at 1606.

Figure 17:
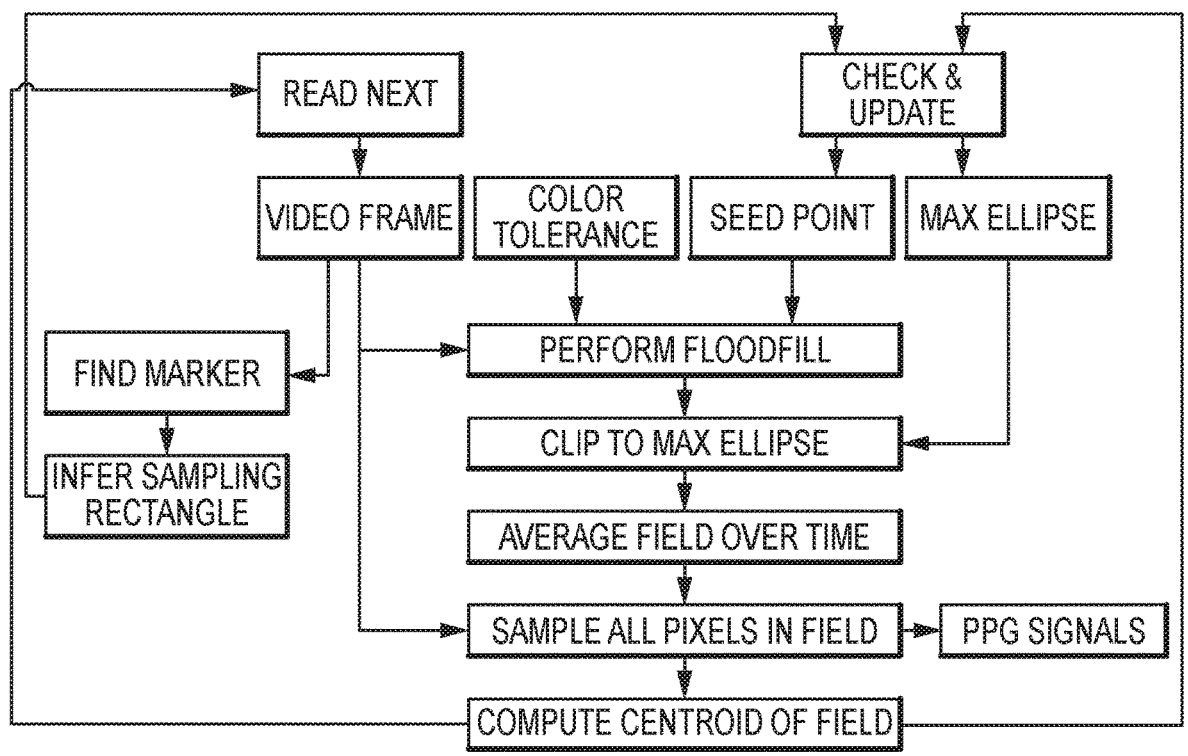
FIG. 17 is a flowchart of a dynamic flood fill method for extracting a light intensity signal, according to an embodiment of the invention.

A flood field algorithm was applied to video signals during a recent clinical study involving healthy human volunteers undergoing a double desaturation protocol. (In this protocol, the volunteers were fitted with a face mask in order to adjust the mixture of oxygen and induce desaturation. Each subject underwent two discrete episodes of hypoxia. Twenty hypoxic episodes were collected from 10 volunteers, spanning a range of skin pigmentations.) A video signal of each subject was acquired during the desaturation episodes. The video image stream was captured using a scientific camera (Basler AcA1920-155uc with Nikon AF-S NIKKOR 35 mm 1:1.8G lens) at a frame rate of 70 fps. A dynamic seed-tracking flood-fill method was utilized to extract the PPG signals from the video. In particular, the method included defining a target rectangle on the subject's forehead, by reference to a forehead sensor on the subject that served as a positional marker. Lower and higher tolerances were set, representing the maximum allowable relative changes between adjacent pixels. A seed point was created at the center of the rectangle, and, for each frame, a floodfill operation was performed which recursively aggregated all adjacent pixels with tolerances, starting from the seed point. The resulting flood field was clipped to an ellipse to create the ROI. Some temporal inertia was applied to reduce flickering around the edges, and then the pixels within the ROI were sampled to extract the PPG signals. A flowchart representing this method is attached in FIG. 17. By repeating this floodfill process for each frame, the flood field is dynamically re-centered even during moderate motion by the subjects.

Figure 18:
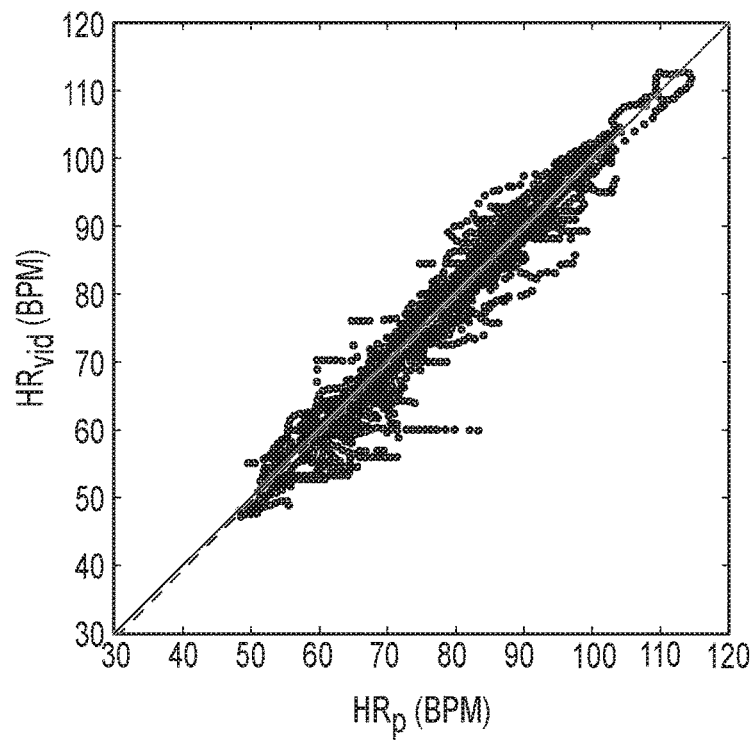
FIG. 18 is a scatter plot of video-derived heart rate versus contact-based oximeter-derived heart rate, showing good agreement between the values.

The dynamically tracking flood field algorithm allowed for a good quality PPG to be generated through moderate motion. Next, the green channel was processed using a fast Fourier transform (FFT) applied over a sliding 30-second temporal window. The video heart rate (HRvid) was computed automatically from the resulting frequency spectra by based on the physiologically relevant local peaks in the spectrum. A Nellcor OxiMax Max-A sensor (Medtronic, Boulder, Colo.) was attached to the subject's finger and provided a reference pulse rate (HRp). FIG. 18 shows a scatter plot of HRvid versus HRp for all the data. The least squares regression line is plotted on the figure, showing good agreement between the video method and the oximeter reference.

The non-contact video monitoring system provides many benefits over traditional contact sensors, and also enables monitoring in new and difficult situations. In one example, the non-contact video-based monitoring system can be used to measure vital signs in patients who are not able to tolerate a contact-based sensor, such as patients with skin trauma. These patients could include burn victims, or patients with other sensitive skin conditions. In another example, the non-contact video-based monitoring system can be used to measure multiple patients at the same time (see FIG. 2B). A method for monitoring two or more patients at the same time includes orienting the field of view of the camera to encompass two or more patients. In an embodiment, the camera is oriented such that the field of view encompasses exposed skin of each patient, and groups of pixels that exhibit physiologic modulations are identified for each respective patient. A single camera system can then be used to measure vital signs from multiple patients, such as patients on a general care floor, or to track movement of patients within a room or ward. Where two or more patients are within a field of view, a skin tone filter may distinguish between different patients by identifying physiologic ROI's that encompass different ranges of color values, due to differences in skin pigmentation of those patients or different lighting conditions across the room. Facial recognition techniques may also be used to distinguish each patient.

In an embodiment, a monitoring system is programmed to take certain steps including activating alarms or messages when a suitable physiologic signal is not ascertainable in the field of view. For example, in an embodiment, a processor acquires a physiologic signal (such as by skin tone filtering or flood filling a region of interest in the field of view, as described above), and determines a physiologic parameter from the signal. However the signal may be lost when the patient moves out of the field of view, or moves in such a way that a physiologic region (such as exposed skin) is not visible, or moves too quickly for accurate tracking. The signal may also be lost if another person or item moves into the field of view and blocks the camera's view of the patient, or if the room becomes too dark (such as if room lights are turned off at night). In any of these or similar situations, the processor starts a timer counting down, and holds the previous value of the calculated physiologic parameter. After a short duration, the processor may send an alert message to be displayed on a screen or otherwise notified to a clinician, to indicate that the signal has been lost and the parameter value is held frozen. If the timer expires, the processor can then sound an alarm or other notification, such as an escalated message or indicator, and remove the frozen physiologic parameter value (or otherwise indicate that it is a previous value, no longer being updated). This can be a system-level alarm or notification, which indicates a problem with the signal acquisition, as distinguished from a physiologic alarm (that would indicate a physiologic parameter of the patient crossing an alarm threshold). This alarm or notification can be a message stating that the room lights have been turned off, or the patient has exited the field of view, or the patient is obscured in the field of view, or the patient is moving, or other applicable circumstance.

This message can be displayed at a remote station (such as a nursing station at a hospital) or on a remote, wireless device (such as a smartphone, tablet, or computer). Additionally, at a central monitoring station (such as a nursing station at a hospital), where display screens display information about multiple different patients, the video-based monitoring system can alert the central station to highlight an individual patient. For example, the remote monitoring system can send an alert or flag based on a change in condition (a system-level alarm, a physiologic alarm, an activity level of the patient, etc), and the central station can then enlarge the video stream from that particular camera. This enables the caregivers at the station to quickly assess the situation in the room and determine if urgent action is needed.

In an embodiment, the processor identifies or is informed that a clinician or caregiver is interacting with the patient, and the processor temporarily halts dynamic tracking of the intensity signal and/or temporarily halts calculation of a physiologic parameter from the intensity signal. This step is taken because such interaction interferes with the camera's view, rendering the light intensity signals more noisy and less reliable. When the interaction is finished, the processor resumes its remote monitoring of the patient.

The vital signs measured from the video signal can be used to trigger alarms based on physiologic limits (for example, high or low heart rate, SpO2, or respiration rate alarms). The video signals, the measured vital signs, and triggered alarms can be used by clinicians to identify patients in distress, provide clinical intervention, apply a treatment, support a diagnosis, or recommend further monitoring. The vital signs measured from the video signals may be further processed to arrive at a final value that can be displayed or compared to alarm limits. Further processing may include adding the vital sign to a running average (such as an infinite impulse response filter) to smooth out variability, rejecting outlier vital sign measurements that are not supported by known physiological limits (such as a newly calculated heart rate that varies by more than a physiologically expected amount, as discussed above), increasing or decreasing a weight applied to the vital sign, calculating statistics relating to the vital sign, or other processing steps. The result is a final number, derived from the vital sign measurement from the intensity signal, and this final derived number can be displayed, stored, or compared to alarm limits.

The systems and methods described here may be provided in the form of tangible and non-transitory machine-readable medium or media (such as a hard disk drive, hardware memory, etc.) having instructions recorded thereon for execution by a processor or computer. The set of instructions may include various commands that instruct the computer or processor to perform specific operations such as the methods and processes of the various embodiments described here. The set of instructions may be in the form of a software program or application. The computer storage media may include volatile and non-volatile media, and removable and non-removable media, for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic disk storage, or any other hardware medium which may be used to store desired information and that may be accessed by components of the system. Components of the system may communicate with each other via wired or wireless communication. The components may be separate from each other, or various combinations of components may be integrated together into a medical monitor or processor, or contained within a workstation with standard computer hardware (for example, processors, circuitry, logic circuits, memory, and the like). The system may include processing devices such as microprocessors, microcontrollers, integrated circuits, control units, storage media, and other hardware.

Although the present invention has been described and illustrated in respect to exemplary embodiments, it is to be understood that it is not to be so limited, since changes and modifications may be made therein which are within the full intended scope of this invention as hereinafter claimed.

What is claimed is:

1. A video-based method of measuring a patient's vital sign, comprising:
    receiving, from a video camera, a video signal having a field of view;
    identifying, using a processor, a first seed point in the field of view;
    flood filling, using the processor, a first contiguous region from the first seed point to a boundary;
    extracting, using the processor, a first intensity signal from the first contiguous region; measuring a vital sign from the first intensity signal; and
    dynamically updating the contiguous region over time, including tracking the first seed point and updating the first contiguous region to create a dynamically morphing contiguous region.

2. The method of claim 1, wherein flood filling the contiguous region comprises identifying, adjacent the first seed point, neighboring pixels or regions that share a common characteristic with the first seed point, until the boundary is reached.

3. The method of claim 2, wherein the boundary comprises pixels that lack the common characteristic.

4. The method of claim 3, wherein the common characteristic comprises color values or intensity values within a range.

5. The method of claim 3, wherein the common characteristic comprises a shared frequency content.

6. The method of claim 1, wherein identifying the first seed point comprises recognizing a facial feature and locating the first seed point relative to the recognized facial feature.

7. The method of claim 6, wherein recognizing a facial feature comprises receiving a user input indicating the facial feature.

8. The method of claim 1, further comprising applying alarm conditions to the displayed number or the first intensity signal, wherein the alarm conditions omit a sensor-off or sensor-disconnect alarm.

9. The method of claim 1, wherein extracting the intensity signal comprises extracting two time-varying color signals, and wherein measuring the vital sign comprises measuring oxygen saturation from the two time-varying color signals.

10. The method of claim 1, wherein identifying the first seed point comprises receiving a user input locating the first seed point.

11. The method of claim 1, wherein the vital sign comprises pulse rate, and wherein measuring the vital sign comprises identifying a frequency content of the intensity signal, and measuring the pulse rate from the frequency content.

12. The method of claim 1, wherein the first seed point comprises a dynamic seed point, and wherein dynamically updating comprises re-generating the contiguous region from the dynamic seed point at a regular time interval.

13. The method of claim 1, wherein the first seed point comprises a dynamic seed point, and wherein dynamically updating comprises re-generating the contiguous region as the dynamic seed point moves within the image frame.

14. The method of claim 1, further comprising subjecting the first seed point or the first contiguous region to a variability criterion, wherein said first seed point or first contiguous region is rejected upon a failure of the variability criterion.

15. The method of claim 14, wherein the failure of the variability criterion indicates a non-physiologic subject.

16. The method of claim 1, further comprising:
    identifying a second seed point on the patient;
    flood filling a second contiguous region from the second seed point;
    utilizing the second contiguous region to extract a second intensity signal;
    measuring a second vital sign from the second intensity signal.

17. The method of claim 16, wherein the first vital sign comprises pulse rate and the second vital sign comprises SpO2.

18. The method of claim 16, wherein the first and second vital signs are both measurements of pulse rate, and further comprising outputting the first vital sign, or the second vital sign, or a combination of both.

19. The method of claim 1, further comprising displaying the first contiguous region.

20. The method of claim 1, wherein the first seed point is located on a patient's forehead, and wherein the boundary comprises an eyebrow region.

* * * * *